US009464079B2

(12) United States Patent
Green et al.

(10) Patent No.: US 9,464,079 B2
(45) Date of Patent: Oct. 11, 2016

(54) TREATMENT OF PROLIFERATIVE DISORDERS WITH A CHEMILUMINESCENT AGENT

(75) Inventors: Bernard S. Green, Jerusalem (IL); Galia Luboshits, Ariel (IL); Michael A. Firer, Ginot Shomron (IL)

(73) Assignees: Semorex Technologies Ltd., Nes Ziona (IL); Ariel-University Research and Development Company Ltd., Ariel (IL)

( * ) Notice: Subject to any disclaimer, the term of this patent is extended or adjusted under 35 U.S.C. 154(b) by 83 days.

(21) Appl. No.: 14/006,733

(22) PCT Filed: Mar. 22, 2012

(86) PCT No.: PCT/IB2012/051373
§ 371 (c)(1),
(2), (4) Date: Sep. 23, 2013

(87) PCT Pub. No.: WO2012/127441
PCT Pub. Date: Sep. 27, 2012

(65) Prior Publication Data
US 2014/0010867 A1    Jan. 9, 2014

Related U.S. Application Data

(60) Provisional application No. 61/466,529, filed on Mar. 23, 2011.

(51) Int. Cl.
| | |
|---|---|
| *C07D 471/04* | (2006.01) |
| *A61K 31/222* | (2006.01) |
| *A61K 31/337* | (2006.01) |
| *A61K 31/473* | (2006.01) |
| *A61K 31/4985* | (2006.01) |
| *A61K 31/502* | (2006.01) |
| *A61K 31/5025* | (2006.01) |
| *A61K 31/661* | (2006.01) |
| *A61K 45/06* | (2006.01) |
| *A61K 38/44* | (2006.01) |
| *A61K 38/17* | (2006.01) |
| *A61K 47/48* | (2006.01) |

(52) U.S. Cl.
CPC .......... *C07D 471/04* (2013.01); *A61K 31/222* (2013.01); *A61K 31/337* (2013.01); *A61K 31/473* (2013.01); *A61K 31/4985* (2013.01); *A61K 31/502* (2013.01); *A61K 31/5025* (2013.01); *A61K 31/661* (2013.01); *A61K 38/1767* (2013.01); *A61K 38/44* (2013.01); *A61K 45/06* (2013.01); *A61K 47/48153* (2013.01); *C12Y 113/12007* (2013.01)

(58) Field of Classification Search
CPC .......... A61K 31/473; A61K 31/4985; A61K 31/502; A61K 31/5025; A61K 38/44; A61K 47/48153; C07D 471/04; C12Y 113/12007
See application file for complete search history.

(56) References Cited

U.S. PATENT DOCUMENTS

| | | | |
|---|---|---|---|
| 4,017,490 A * | 4/1977 | Yurugi ................. | C07D 213/80 514/869 |
| 5,094,939 A | 3/1992 | Okada et al. | |
| 5,420,275 A | 5/1995 | Masuya et al. | |
| 5,543,410 A | 8/1996 | Minin et al. | |
| 6,204,266 B1 | 3/2001 | Rees | |
| 6,376,525 B1 | 4/2002 | Kong | |
| 7,772,179 B2 | 8/2010 | Firer et al. | |
| 7,960,384 B2 * | 6/2011 | Feng .................. | C07D 215/227 514/252.1 |
| 2006/0286170 A1 | 12/2006 | Kong | |
| 2007/0112061 A1 | 5/2007 | Kimura et al. | |
| 2009/0054306 A1 * | 2/2009 | Firer .................. | A61K 41/0071 514/1.1 |

FOREIGN PATENT DOCUMENTS

| | | |
|---|---|---|
| EP | 0491477 | 6/1992 |
| EP | 491477 A1 * | 6/1992 |
| JP | 03-261467 | 11/1991 |

(Continued)

OTHER PUBLICATIONS

Chien, A.J.; Moasser, M.M. "Cellular Mechanisms of Resistance to Anthracyclines and Taxanes in Cancer: Intrinsic and Acquired" Seminars in Oncology, vol. 35, No. 2, Suppl 2, Apr. 2008, pp. S1-S14.*
Denner, L.A.; Dixon, R.A.F. Annual Reports in Medicinal Chemistry 1995, 30, 61-70.*
Hricik, D.E.; Chung-Park, M.; Sedor, J.R. "Glomerulonephritis" The New England Journal of Medicine 1998, 339, 13, 888-899.*
Hall, I.H.; Hall, E.S.; Wong, O.T. "The anti-neoplastic activity of 2,3-dihydrophthalazine-1,4-dione and N-butyl-2,3-dihydrophthalazine-1,4-dione in human and murine tumor cells" Anti-Cancer Drugs, 1992, 3, 55-62.*
Tannous, B.A. "Gaussia luciferase reporter assay for monitoring of biological processes in culture and in vivo" Nat Protoc. 2009 ; 4(4): 582-591.*

(Continued)

*Primary Examiner* — Timothy Thomas
*Assistant Examiner* — Andrew S Rosenthal

(57) ABSTRACT

Methods employing chemiluminescent agents as therapeutically active agents in the treatment of proliferative disorders are disclosed. The chemiluminiscent agents are used in the disclosed method without a therapeutically effective amount of a photosensitizer. Novel chemiluminescent agents having the general formula:

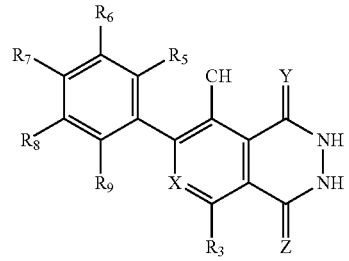

are also disclosed, wherein X, Y, Z, $R_3$ and $R_5$-$R_9$ are as defined herein.

11 Claims, 8 Drawing Sheets

(56) References Cited

FOREIGN PATENT DOCUMENTS

| RU | 2370263 | 10/2009 |
|---|---|---|
| RU | 2370264 | 10/2009 |
| WO | WO 00/71129 | 11/2000 |
| WO | WO 01/82780 | 11/2001 |
| WO | WO 2005/034955 | 4/2005 |
| WO | WO 2006/032518 | 3/2006 |
| WO | WO 2007/081630 | 7/2007 |
| WO | WO 2007/112347 | 10/2007 |
| WO | WO 2009/028543 | 3/2009 |
| WO | WO 2010/062787 | 6/2010 |
| WO | WO 2010/147917 | 12/2010 |
| WO | WO 2012/127441 | 9/2012 |

OTHER PUBLICATIONS

Lee at al. "In vivo imaging of hydrogen peroxide with chemiluminescent nanoparticles" Nat Matl 2007, 6, 765-769.*
Lim et al. "IncreasedNox1andHydrogen Peroxide in Prostate Cancer" The Prostate 2005, 62:200-207.*
Park, J.W. "Liposome-based drug delivery in breast cancer treatment" Breast Cancer Res 2002, 4:95-99.*
Li, M. et al. "Improved Enzyme Immunoassay for Human Basic Fibroblast Growth Factor Using a New Enhanced Chemiluminescence System" Biochemical and Biophysical Research Communications 1993, 193 (2), 540-545.*
Communication Relating to the Results of the Partial International Search Dated May 25, 2012 From the International Searching Authority Re. Application No. PCT/IB2012/051373.
International Search Report and the Written Opinion Dated Aug. 31, 2012 From the International Searching Authority Re. Application No. PCT/IB2012/051373.
Abidov et al. "Effects of Tamerit on Metastasis From Mouse Melanoma B16", International Journal of Cancer, Supplement, XP008154997, p. 160, # 56, Jan. 1, 2002. Abstract.
Carpenter et al. "Chemilumenescent Activation of the Antiviral Activity of Hypericin: A Molecular Flashlight", Proc. Natl. Acad. Sci. USA, 91: 12273-12277, Dec. 1994.
Hall et al. "The Anti-Neoplastic Activity of 2,3-Dihydrophthalazine-1,4-Dione in Human and Murine Tumor Cells", Anti Cancer Drugs, XP008154852, 3(1): 55-62, Feb. 1, 1992. Abstract, Fig.1, Tables 1-4, p. 56, r-h col., Para 2, p. 61, col. 3, Last Para.
Jiang et al. "Retrovirus-Induced Oxidative Stress With Neuroimmunodegeneration Is Suppressed by Antioxidant Treatment With A Refined Monosodium α-Luminol (Galavit)", Journal of Virology, 80(9): 4557-4569, May 2006.
Omura et al. "Studies on the Syntheses of N-Heterocyclic Compounds. XXVIII. Syntheses of Pyrido[3,4-d]Pyridazine Derivatives", Chemical & Pharmaceutical Bulletin, XP002682107, 24(11: 2699-2710, 1976. Compounds 5, 12, 17, 24, 33.
Patrone et al. "Chemiluminescent Solid Lipid Nanoparticles and Interactions With Intact Skin", The John Hopkins University Applied Physics Laboratory, 2007, Last Verified Dec. 30, 2010.
Phillip et al. "Chemiluminescence and Hematoporphyrin Derivative: A Novel Therapy for Mammary Adenocarcinomas in Mice", Oncology, 46: 266-272, 1989.
Theodossiou et al. "Firefly Luciferin-Activated Rose Bengal: In Vitro Photodynamic Therapy by Intracellular Cehmiluminescence in Transgenic NIH 3T3 Cells", Cancer Research, 63: 1818-1821, Apr. 15, 2003.
International Preliminary Report on Patentability Dated Oct. 3, 2013 From the International Bureau of WIPO Re. Application No. PCT/IB2012/051373.
Office Action Dated May 1, 2016 From the Israel Patent Office Re. Application No. 228593 and Its Translation Into English.
Patent Examination Report Dated May 20, 2016 From the Australian Government, IP Australia Re. Application No. 2012232670.

* cited by examiner

SEM-009

SEM-010

SEM-011

SEM-012

SEM-013

SEM-014

SEM-007 (L012)

TREATMENT OF PROLIFERATIVE DISORDERS WITH A CHEMILUMINESCENT AGENT

RELATED APPLICATIONS

This application is a National Phase of PCT Patent Application No. PCT/IB2012/051373 having International filing date of Mar. 22, 2012, which claims the benefit of priority under 35 USC §119(e) of U.S. Provisional Patent Application No. 61/466,529 filed on Mar. 23, 2011. The contents of the above applications are all incorporated by reference as if fully set forth herein in their entirety.

FIELD AND BACKGROUND OF THE INVENTION

The present invention, in some embodiments thereof, relates to therapy, and more particularly, but not exclusively, to novel methods of treating proliferative disorders.

Chemiluminescence is light resulting from a chemical reaction which produces an intermediate in an excited electronic state. The excited intermediate decays into an electronic ground state through fluorescence or phosphorescence, depending on the spin state of the excited intermediate, thereby producing light.

Chemiluminescence may be produced by a variety of structurally unrelated compounds.

FIG. 1 presents the chemical structures of representative members of some families of chemiluminescent compounds.

Some compounds emit chemiluminescence upon oxidation, for example, via reaction with reactive oxygen species (ROS).

One family of such compounds comprises compounds having a 1,2-dihydropyridazine-3,6-dione moiety, such as derivatives of 2,3-dihydrophthalazine-1,4-dione (e.g., luminol, isoluminol) and 2,3-dihydropyridopyridazine-1,4-dione (e.g., L-012) (see, FIG. 1).

U.S. Pat. No. 5,420,275 and European Patent Application EP 01491477 describe chemiluminescent pyridopyridazine compounds such as L-012, and uses thereof for assays.

Coelenterazines such as CLA and MCLA (see, FIG. 1) also produce chemiluminescence upon reacting with ROS.

Lucigenin (see, FIG. 1) represents another family of compounds which produce chemiluminescence upon reacting with ROS.

In a somewhat different mechanism, oxalate derivatives produce chemiluminescence in combination with a fluorescent molecule. Upon reacting with ROS, oxalates are oxidized to produce a 1,2-dioxetanedione intermediate. This intermediate decomposes while transferring energy to a fluorescent compound, which then emits light. The emission wavelength can be controlled by selecting different fluorescent compounds.

Some compounds produce chemiluminescence when acted upon by a suitable enzyme.

For example, chemiluminescence may be produced by firefly luciferin in the presence of ATP, luciferase and magnesium ion.

In addition, stable dioxetane compounds may decompose when acted upon by a specific enzyme, thereby producing chemiluminescence.

U.S. Pat. No. 5,094,939 describes stabilized dioxetane derivatives comprising a phosphate moiety, which decompose following cleavage of the phosphate moiety by a phosphatase, generating products which emit chemiluminescence. AMPPD (disodium 3-(4-methoxyspiro{1,2-dioxetane-3,2'-(5'-chloro)tricyclo [3.3.1.1]decan}-4-yl)phenyl phosphate; also referred to in the art as "CSPD") is described therein as an example of a stabilized dioxetane derivative (see, FIG. 1).

Similarly, dioxetane derivatives have been prepared, which produce chemiluminescence when hydrolysed by a peptidase [Richard et al., *Organic Letters* 2007, 9:4853: 4855].

Chemiluminescence in the presence of a photosensitizer has been used to activate photosensitizers in order to destroy cells.

U.S. Pat. No. 7,772,179 describes methods utilizing a chemiluminescent agent and a conjugate comprising a photosensitizer linked to a transport ligand, for selectively destroying target cells and for treating a disorder associated with undesired activity of a cell population. The methods are exemplified therein by the use of a transferrin-hematoporphyrin conjugate with luminol as a chemiluminescent agent.

Carpenter et al. [*Proc Natl Acad Sci USA* (1994) 91:12273-12277] describes the use of a luciferin/luciferase reaction for activating a hypericin photosensitizer, and the subsequent destruction of equine dermal cells.

Theodossiou et al. [*Cancer Res* (2003) 63:1818-1821] describes the use of a luciferin/luciferase reaction for activating a rose bengal photosensitizer in luciferase transfected murine fibroblasts.

Phillip et al. [*Oncology* (1989) 46:266-272] describes an attempt to use the photosensitizer Photofrin II in combination with a chemiluminescent system comprising substituted oxamide, rubrene, a surfactant, and hydrogen peroxide, in order to treat tumors in mice. The results presented therein show that the anti-tumor effect is not dependent on light emission.

Refined monosodium luminol is sold under the trade name Galavit™, and exhibits antioxidant properties which may be useful for treating disorders associated with oxidative stress [Jiang et al., *J Virol* 2006, 80:4557-4569]. There have been controversial claims that Galavit™ can be used to treat cancer, but these claims have not been substantiated, and have even resulted in criminal convictions for selling a fraudulent cancer cure [Tuffs, *BMJ* 2008, 337:a875].

Additional background art includes International Patent Application PCT/US2009/063186 (published as WO 2010/062787), International Patent Application PCT/US2007/064919 (published as WO 2007/112347), International Patent Application PCT/JP2008/065286 (published as WO 2009/028543), International Patent Application PCT/US2006/061890 (published as WO 2007/081630), International Patent Application PCT/US2001/13730 (published as WO 2001/082780), U.S. Patent Application Publication No. 2006/0286170, U.S. Pat. No. 6,376,525, International Patent Application PCT/US2000/13420 (published as WO 2000/71129), International Patent Application PCT/US2010/038568 (published as WO 2010/147917), Russian Patent No. 2370264, International Patent Application PCT/EP2005/010311 (published as WO 2006/032518), International Patent Application PCT/US2003/032612 (published as WO 2005/034955), and Japanese Patent Application No. 19900061694 (published as JP 326147).

SUMMARY OF THE INVENTION

The present inventors have now surprisingly uncovered that some chemiluminescent agents can be utilized for destroying tumor cells, even when utilized per se, namely, without an effective amount of a photosensitizer.

Thus, novel methodologies for treating proliferative diseases and disorders are disclosed herewith.

In some embodiments, the methodologies described herein do not comprise a use of a photosensitizer in addition to the chemiluminescent agent. As exemplified herein, a chemiluminescent agent may exhibit an effective anti-tumor activity in the absence of a photosensitizer.

In alternative embodiments, the methodologies described herein comprise a use of a photosensitizer in addition to the chemiluminescence agent. In such embodiments, a small amount of the photosensitizer is used, which is not sufficient to be therapeutically effective via activation of the photosensitizer per se. However, the photosensitizer may act in synergy with the chemiluminescent agent, so as to increase anti-tumor activity of the chemiluminescent agent. Such synergy may allow even a small amount of a photosensitizer to exhibit a therapeutically effective activity.

According to an aspect of some embodiments of the invention, there is provided a method of treating a proliferative disease or disorder in a subject in need thereof, the method comprising administering to the subject a chemiluminescent agent, thereby treating the proliferative disease or disorder, the method being devoid of administering a therapeutically effective amount of a photosensitizer in combination with the chemiluminescent agent.

According to an aspect of some embodiments of the invention, there is provided a use of a chemiluminescent agent in the manufacture of a medicament for use in the treatment of a proliferative disease or disorder, wherein the treatment is devoid of using a therapeutically effective amount of a photosensitizer in combination with the chemiluminescent agent.

According to an aspect of some embodiments of the invention, there is provided a chemiluminescent agent, being identified for use in the treatment of a proliferative disease or disorder, wherein the treatment is devoid of using a therapeutically effective amount of a photosensitizer in combination with the chemiluminescent agent.

According to an aspect of some embodiments of the invention, there is provided a pharmaceutical composition comprising a chemiluminescent agent and a pharmaceutically acceptable carrier, the composition being packaged is a packaging material and identified in print, in or on the packaging material, for use in the treatment of a proliferative disease or disorder, wherein the treatment is devoid of using a therapeutically effective amount of a photosensitizer in combination with the chemiluminescent agent.

According to an aspect of some embodiments of the invention, there is provided a method of treating a proliferative disease or disorder in a subject in need thereof, the method comprising administering to the subject a therapeutically effective amount of a compound having the general formula:

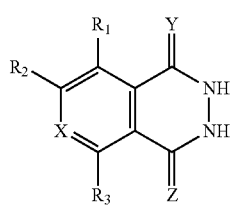

wherein:
X is N or $CR_4$;
Y and Z are each independently O or S; and $R_1$-$R_4$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of $R_1$-$R_4$ form a five- or six-membered alicyclic or aromatic ring, thereby treating the proliferative disease or disorder.

According to an aspect of some embodiments of the invention, there is provided a use of a compound having the general formula:

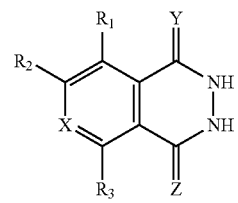

wherein:
X is N or $CR_4$;
Y and Z are each independently O or S; and
$R_1$-$R_4$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of $R_1$-$R_4$ form a five- or six-membered alicyclic or aromatic ring, in the manufacture of a medicament for use in the treatment of a proliferative disease or disorder.

According to an aspect of some embodiments of the invention, there is provided a compound having the general formula:

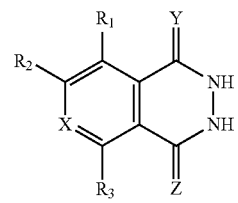

wherein:
X is N or $CR_4$;
Y and Z are each independently O or S; and $R_1$-$R_4$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of $R_1$-$R_4$ form a five- or six-membered alicyclic or aromatic ring, being identified for use in the treatment of a proliferative disease or disorder.

According to an aspect of some embodiments of the invention, there is provided a pharmaceutical composition comprising a compound having the general formula:

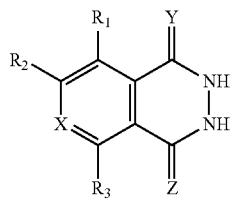

wherein:

X is N or CR$_4$;

Y and Z are each independently O or S; and

R$_1$-R$_4$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of R$_1$-R$_4$ form a five- or six-membered alicyclic or aromatic ring, and a pharmaceutically acceptable carrier, the composition being packaged in a packaging material and identified in print, in or on the packaging material, for use in the treatment of a proliferative disease or disorder.

According to an aspect of some embodiments of the invention, there is provided a compound having the general formula:

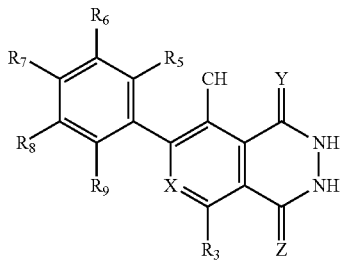

wherein:

X is N or CR$_4$;

Y and Z are each independently O or S; and

R$_3$-R$_9$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of R$_3$-R$_9$ form a five- or six-membered alicyclic or aromatic ring, wherein at least one of R$_3$, R$_5$, R$_7$ and R$_9$ is selected from the group consisting of aryl, heteroaryl, halo, hydroxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino.

According to an aspect of some embodiments of the invention, there is provided a conjugate comprising a chemiluminescent agent described herein or a compound described herein, covalently linked to a targeting moiety, the conjugate being identified for use in the treatment of a proliferative disease or disorder.

According to an aspect of some embodiments of the invention, there is provided a liposome comprising a chemiluminescent agent described herein or a compound described herein, the liposome being identified for use in the treatment of a proliferative disease or disorder.

According to some embodiments, the method is devoid of administering a photosensitizer in combination with the chemiluminescent agent.

According to some embodiments, the method is devoid of administering a photosensitizer in combination with the compound.

According to some embodiments, the method is devoid of administering a therapeutically effective amount of a photosensitizer in combination with the compound.

According to some embodiments, the treatment is devoid of using a photosensitizer in combination with the chemiluminescent agent.

According to some embodiments, the treatment is devoid of using a photosensitizer in combination with the compound.

According to some embodiments, the treatment is devoid of using a therapeutically effective amount of a photosensitizer in combination with the compound.

According to some embodiments, the chemiluminescent agent is selected from the group consisting of a coelenterazine, a chemiluminescent agent comprising a 1,2-dioxetane moiety, a chemiluminescent agent comprising a 1,2-dihydropyridazine-3,6-dione moiety, a lucigenin, a luciferin/luciferase combination, and an oxalate in combination with a dye.

According to some embodiments, the chemiluminescent agent comprises a 1,2-dihydropyridazine-3,6-dione moiety having the general formula:

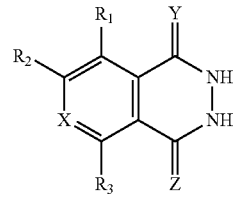

wherein:

X is N or CR$_4$;

Y and Z are each independently O or S; and

R$_1$-R$_4$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of R$_1$-R$_4$ form a five- or six-membered alicyclic or aromatic ring.

According to some embodiments, X is N.

According to some embodiments, $R_2$ is a substituted or non-substituted aryl.

According to some embodiments, $R_3$ is selected from the group consisting of hydrogen, hydrazine and halo.

According to some embodiments, $R_1$ is selected from the group consisting of hydroxy and amino.

According to some embodiments, the coelenterazine has the general formula:

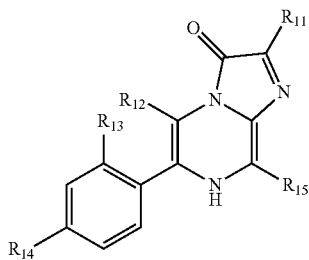

wherein:

$R_{11}$-$R_{15}$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino.

According to some embodiments, the chemiluminescent agent comprising a 1,2-dioxetane moiety has the general formula:

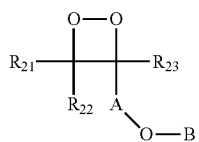

wherein:

$R_{21}$ is selected from the group consisting of substituted or non-substituted cycloalkyl and heteroalicyclic, and $R_{22}$ is hydrogen; or $R_{21}$ and $R_{22}$ together form a substituted or non-substituted cycloalkyl or heteroalicyclic ring;

$R_{23}$ is alkoxy;

A is selected from the group consisting of substituted or non-substituted aryl and heteroaryl; and B is a moiety capable of being cleaved by an enzyme present in situ.

According to some embodiments, the luciferase is selected from the group consisting of firefly luciferase, *Latia* luciferase, *Omphalotus* luciferase, *Renilla* luciferase, bacterial luciferase, and aequorin.

According to some embodiments, the chemiluminescent agent is coupled to a targeting moiety.

According to some embodiments, the chemiluminescent agent is encapsulated by a liposome.

According to some embodiments, the compound is coupled to a targeting moiety.

According to some embodiments, the compound is encapsulated by a liposome.

According to some embodiments, the liposome comprises a targeting moiety attached to a surface thereof.

According to some embodiments, the method further comprises administering at least one additional agent which is effective for treating the proliferative disease or disorder.

According to some embodiments, the treatment further comprises using at least one additional agent which is effective for treating the proliferative disease or disorder.

According to some embodiments, at least one of $R_3$, $R_5$, $R_7$ and $R_9$ is selected from the group consisting of halo and hydrazine.

According to some embodiments, $R_5$-$R_9$ are each hydrogen.

According to some embodiments, $R_3$ is hydrogen.

According to some embodiments, $R_5$ and $R_7$ are selected from the group consisting of halo and hydrogen, and $R_6$, $R_8$ and $R_9$ are each hydrogen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to therapy, and more particularly, but not exclusively, to novel methods of treating proliferative disorders.

Some embodiments of the present invention are based on the findings that some chemiluminescent agents can be utilized for destroying tumor cells, even when utilized per se, namely, without an effective amount of a photosensitizer. These findings are particularly surprising in view of the assumption of previous reports that any anti-tumor effect of chemiluminescent agents is merely derived from use of chemiluminescent agents as a light source for activating a photosensitizer which exhibits the anti-tumor effect.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 1:
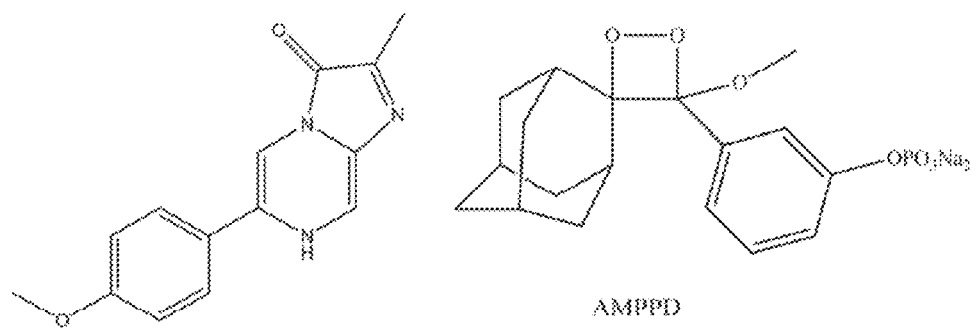
FIG. 1 is a scheme depicting representative members of some families of chemiluminescent compounds.
Figure 1:
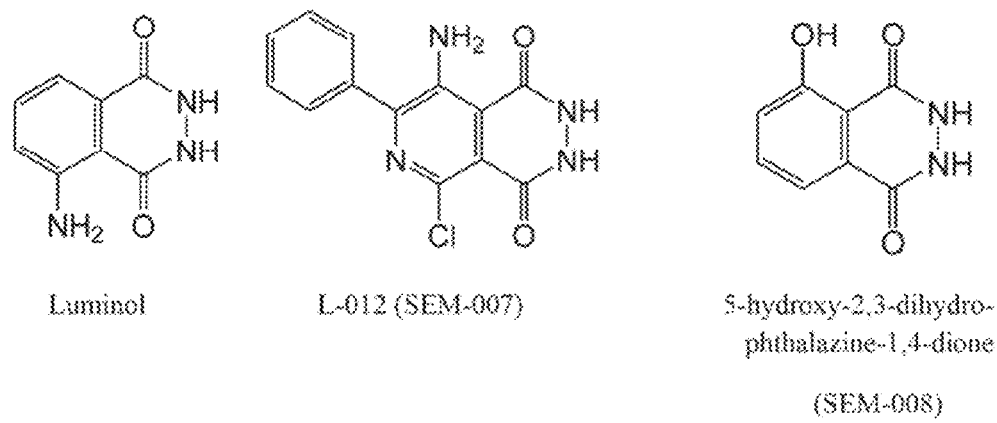
Figure 1:
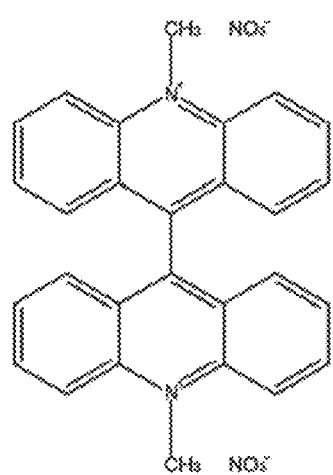
Figure 1:
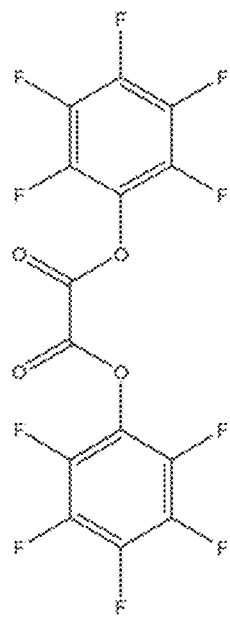
Figure 6:
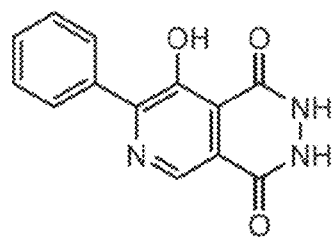
FIG. 6 is a scheme depicting exemplary 2,3-dihydropyridopyridazine-1,4-dione compounds.
Figure 6:
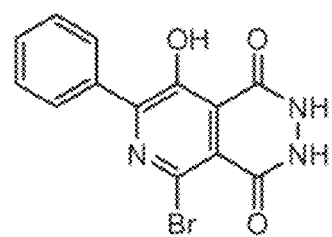
Figure 6:
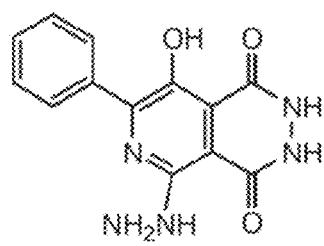
Figure 6:
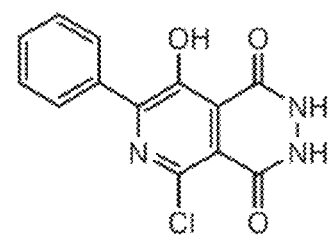
Figure 6:
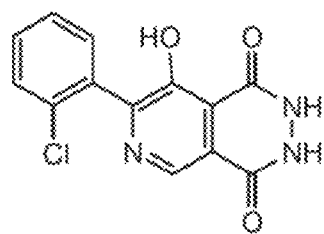
Figure 6:
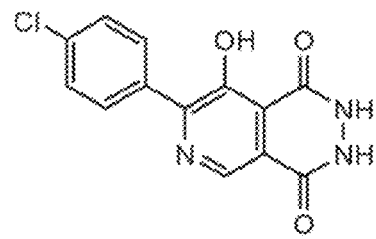
Figure 6:
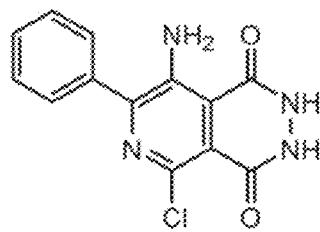

FIG. 1 depicts representative members of some families of chemiluminescent compounds, as classified according to structural features. FIG. 6 depicts exemplary compounds having a 2,3-dihydropyridopyridazine-1,4-dione core. Such compounds may be considered as belonging to a family of chemiluminescent agents.

FIGS. 2-4B show an anti-proliferative effect of the chemiluminescent agent L-012 (also referred to herein as "SEM-007") on prostate cancer cells injected into mice, in a dose dependent manner. Tumor volume was reduced by up to 95%. FIG. 5 shows that L-012 inhibited tumor-induced weight loss in the mice, in a dose dependent manner.

Figure 7:
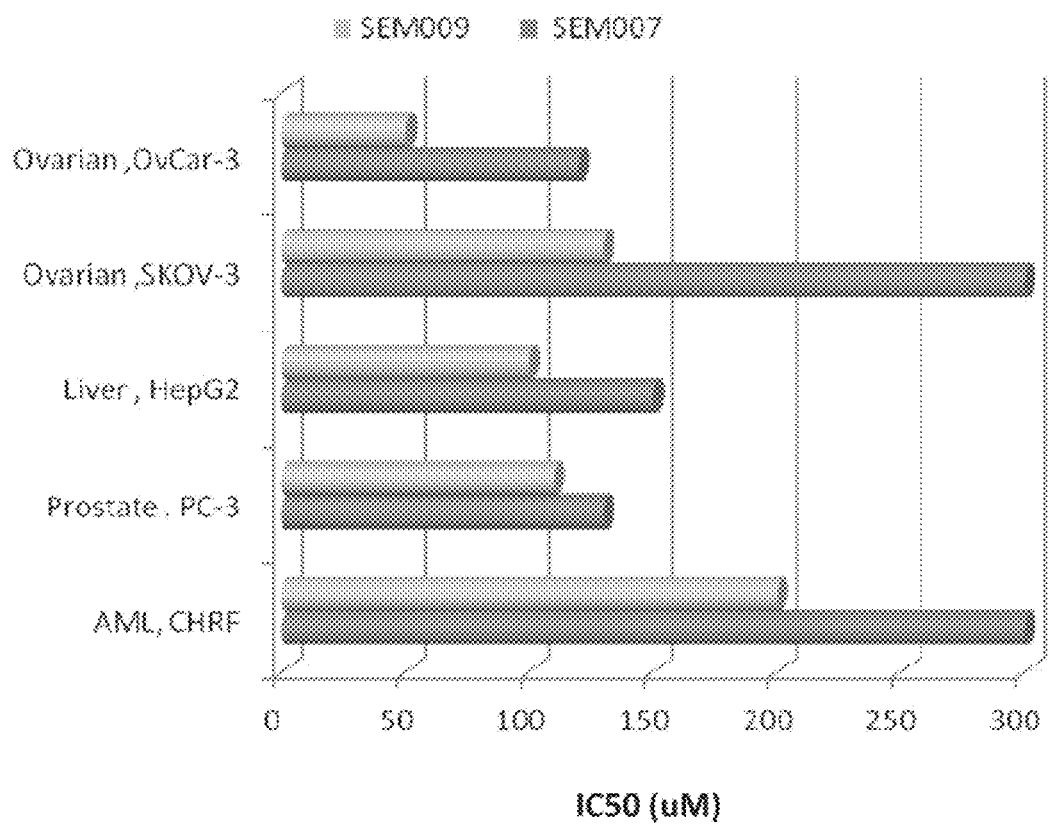
FIG. 7 is a bar graph showing the IC50 concentration of the exemplary compounds SEM-007 and SEM-009 in OvCar-3 ovarian cancer cells, SKOV-3 ovarian cancer cells, HepG2 liver cancer cells, PC-3 prostate cancer cells, and CHRF acute myeloid leukemia cells.

Table 1 and FIG. 7 show the dose-dependent anti-proliferative efficacy of exemplary compounds having a 2,3-dihydropyridopyridazine-1,4-dione core (in addition to L-012). FIG. 7 shows that an exemplary compound (SEM-009) is more potent than SEM-007 (L-012) in a variety of cancer cell types.

Table 2 shows that additional chemiluminescent agents (which do not include a 2,3-dihydropyridopyridazine-1,4-dione core) also exhibit anti-proliferative activity, indicating that this is a general property shared by many chemiluminescent agents.

Table 3 summarizes the data obtained in in vitro studies conducted with PC-3 cells cultured for various time periods with different concentrations of various chemiluminescent compounds, showing the growth inhibition of cells by the various chemiluminescent agents tested.

Figure 8:
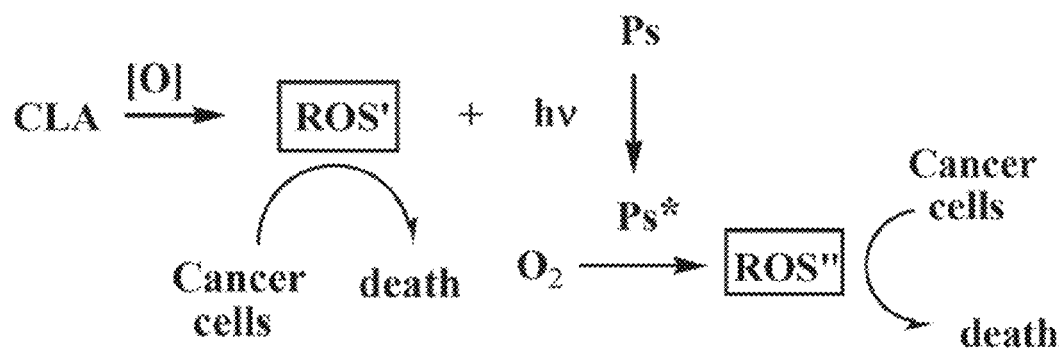
FIG. 8 is a scheme depicting a therapeutic mechanism according to optional embodiments of the invention, wherein a chemiluminescent agent (CLA) is oxidized to produce reactive oxygen species (ROS'), which cause death of cancer cells, as well as light, which excites a photosensitizer (Ps) to an excited state (Ps*); the excited state of the photosensitizer reacts with $O_2$ to produce additional reactive oxygen species (ROS"), which enhances the death of cancer cells.

FIG. 8 presents a therapeutic mechanism according to some embodiments of the invention, wherein a chemiluminescent agent (CLA) causes death of cancer cells in combination with a small amount of photosensitizer (e.g., a synergistic combination).

The abovementioned results indicate that anti-proliferative activity is a general property shared by many chemiluminescent agents, such as, for example, SEM-009 and structurally related compounds, and that such chemiluminescent agents may therefore be useful for treating proliferative diseases and disorders, including cancer.

Hence, according to an aspect of some embodiments of the invention, there is provided a method of treating a proliferative disease or disorder in a subject in need thereof, the method comprising administering to the subject a chemiluminescent agent, thereby treating the proliferative disease or disorder.

According to some embodiments, the treatment is devoid of using a therapeutically effective amount of a photosensitizer in combination with the chemiluminescent agent, as is detailed hereinbelow.

The phrase "devoid of using (or administering) a therapeutically effective amount of a photosensitizer in combination with the chemiluminescent agent", as used herein, means that a photosensitizer is not administered to a treated subject during the treatment with the chemiluminescent agent in such a way that the light produced by the chemiluminescent agent activates the photosensitizer and in such a way that this activation of the photosensitizer per se can destroy target cells and/or treat the disease or disorder. Thus, this phrase encompasses any of the following: (i) no photosensitizer is administered to a treated subject during the treatment with the chemiluminescent agent; and (ii) a photosensitizer that can be activated by the light produced by the chemiluminescent agent is not administered to a treated subject during the treatment with the chemiluminescent agent; and (iii) a photosensitizer that can be activated by the light produced by the chemiluminescent agent is administered to a treated subject during the treatment with the chemiluminescent agent, but not in such an amount that this activation of the photosensitizer per se can destroy target cells and/or treat the disease or disorder.

According to some embodiments, the treatment is devoid of using a photosensitizer in combination with the chemiluminescent agent, that is, a photosensitizer (or a photosensitizer that can be activated by the light produced by the chemiluminescent agent) is not administered to a treated subject during the treatment with the chemiluminescent agent.

It is to be understood that the phrase "chemiluminescent agent", as used herein, encompasses both individual compounds which may emit chemiluminescent light, and chemiluminescent systems which comprise a plurality of compounds which in combination may emit chemiluminescent light (e.g., an oxalate in combination with a dye, a luciferin in combination with a luciferase). Thus, the term "agent" is used herein in the singular for the sake of simplicity, and is not intended to imply the presence of only one compound.

In any of the methods and uses described herein a therapeutically effective amount of the chemiluminescent agent is utilized.

As used herein, a "therapeutically effective amount" means an amount of an active ingredient (e.g., chemiluminescent agent or photosensitizer) which is effective to treat a proliferative disorder, as defined herein, alleviate or ameliorate symptoms of a proliferative disorder, and/or prolong the survival of the subject being treated.

According to some embodiments, the chemiluminescent agent reacts to produce chemiluminescent light upon reaction with a reactive oxygen species present in situ. Such agents are referred to herein also as ROS-activated chemiluminescent agents.

According to some embodiments of the invention, the chemiluminescent agent reacts to produce chemiluminescent light upon activation by an enzyme present in situ (e.g., a phosphatase, a glycosidase, a peptidase, a luciferase).

According to some embodiments, reaction of the chemiluminescent agent (e.g., a reaction which may produce chemiluminescent light), such as, for example, reaction with ROS in situ or upon activation by an enzyme in situ, is associated with the production of ROS. Optionally, the chemiluminescent agent reacts with ROS in situ so as to produce a greater amount of ROS and/or a more reactive type of ROS. Such agents are referred to herein also as ROS-producing chemiluminescent agents.

As noted hereinabove, a photosensitizer that can be activated by the light produced by the chemiluminescent agent may, in some embodiments, be administered to a treated subject during the treatment with the chemiluminescent agent, but not in such an amount that this activation of the photosensitizer per se can destroy target cells and/or treat the disease or disorder.

Thus, in some embodiments, a photosensitizer is co-administered with the chemiluminescent agent, yet, the amount of a photosensitizer that can be activated by the light produced by the chemiluminescent agent at the target cells is substantially lower than a therapeutically effective amount of the photosensitizer.

Without being bound by any particular theory, it is suggested that in cases where an amount of a photosensitizer that can be activated by the light produced by the chemiluminescent agent at the target cells is substantially lower than a therapeutically effective amount of the photosensitizer, such a low amount may optionally be sufficient to contribute to a therapeutic effect, for example, by enhancing an activity (e.g., ROS production) of a ROS-activated chemiluminescent agent and/or by resulting is a cumulative ROS-producing effect by both the photosensitizer and a ROS-producing chemiluminescent agent.

Thus, according to optional embodiments, oxidation of the chemiluminescent agent produces ROS and light, and the light excites a low amount of photosensitizer which is present, thereby producing additional ROS, as depicted in FIG. 8.

In some embodiments, a photosensitizer acts in synergy with the chemiluminescent agent.

Optionally, the chemiluminescent agent is combined with an oxidizing agent (e.g., hydrogen peroxide).

Optionally, the chemiluminescent agent is combined with a photosensitizer (e.g., a small amount of a photosensitizer, as described hereinabove) which enhances oxidation of the chemiluminescent agent and/or which acts in synergy with the chemiluminescent agent.

According to some embodiments of the invention, the method or treatment described further comprises using (e.g., administering, using to prepare a medicament) at least one additional agent which is effective for treating the proliferative disease or disorder (e.g., an anti-cancer agent). In some embodiments, the additional agent does not include a photosensitizer in a therapeutically effective amount, as defined herein.

Exemplary chemiluminescent agents that are suitable for use in the context of embodiments of the present invention include, but are not limited to, coelenterazines, chemiluminescent agents comprising a 1,2-dioxetane moiety, chemiluminescent agents comprising a 1,2-dihydropyridazine-3,6-dione moiety, lucigenins (e.g., bis-N-methylacridinium nitrate, or a derivative and/or analog thereof), a luciferin/luciferase combination, and oxalates in combination with a dye. Any other compounds that act as chemiluminescent agents, via the above-described or any other mechanism of action, are also contemplated.

According to some embodiments of the invention, chemiluminescent agent comprising a 1,2-dihydropyridazine-3,6-dione moiety can be represented by the general formula:

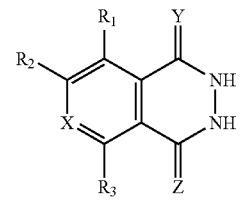

wherein:
X is N or CR$_4$;
Y and Z are each independently O or S; and
R$_1$-R$_4$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, or, alternatively, any two of R$_1$-R$_4$ form a five- or six-membered alicyclic or aromatic ring.

In some embodiments, the alkyl, cycloalkyl, heteroalicyclic, aryl and heteroaryl are non-substituted.

Optionally, the chemiluminescent agent is not luminol or isoluminol.

According to some embodiments of the invention, X is N.

According to some embodiments of the invention, R$_2$ is substituted or non-substituted aryl (e.g., phenyl, substituted phenyl). In exemplary embodiments, R$_2$ is non-substituted phenyl.

According to some embodiments of the invention, R$_3$ is selected from the group consisting of hydrogen, hydrazine, and halo.

Chloro and bromo are exemplary halo atoms.

Non-substituted hydrazine (i.e., —NH—NH$_2$) is an exemplary hydrazine group.

According to some embodiments of the invention, R$_1$ is selected from the group consisting of hydroxy and amino. In some embodiments, R$_1$ is hydroxy.

Non-substituted amino (i.e., —NH$_2$) is an exemplary amino group.

In some embodiments, X is N, and R$_2$ is substituted or non-substituted aryl (phenyl in some embodiments).

In some embodiments, X is N, and R$_3$ is selected from the group consisting of hydrogen, hydrazine, and halo (e.g., as these groups are described herein).

In some embodiments, X is N, and R$_1$ is selected from the group consisting of hydroxy and amino (—NH$_2$ in some embodiments). In some embodiments, R$_1$ is hydroxy.

In some embodiments, R$_2$ is substituted or non-substituted aryl (phenyl in some embodiments), and R$_3$ is selected from the group consisting of hydrogen, hydrazine, and halo (e.g., as these groups are described herein).

In some embodiments, R$_2$ is substituted or non-substituted aryl (phenyl in some embodiments), and R$_1$ is selected from the group consisting of hydroxy and amino. In some embodiments, R$_1$ is hydroxy.

In some embodiments, R$_3$ is selected from the group consisting of hydrogen, hydrazine, and halo (e.g., as these groups are described herein), and R$_1$ is selected from the group consisting of hydroxy and amino. In some embodiments, R$_1$ is hydroxy.

In some embodiments, X is N, R$_2$ is substituted or non-substituted aryl (phenyl in some embodiments), and R$_3$ is selected from the group consisting of hydrogen, hydrazine, and halo (e.g., as these groups are described herein).

In some embodiments, X is N, R$_2$ is substituted or non-substituted aryl (phenyl in some embodiments), and R$_1$ is selected from the group consisting of hydroxy and amino. In some embodiments, R$_1$ is hydroxy.

In some embodiments, X is N, R$_3$ is selected from the group consisting of hydrogen, hydrazine, and halo (e.g., as these groups are described herein), and R$_1$ is selected from the group consisting of hydroxy and amino. In some embodiments, R$_1$ is hydroxy.

In some embodiment, R$_2$ is substituted or non-substituted aryl (phenyl in some embodiments), R$_1$ is selected from the group consisting of hydroxy and amino, and R$_3$ is selected from the group consisting of hydrogen, hydrazine, and halo (e.g., as these groups are described herein). In some embodiments, R$_1$ is hydroxy.

According to some embodiments of the invention, coelenterazines as described herein can be collectively represented by the general formula:

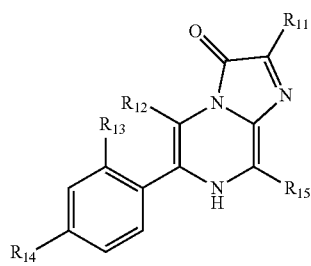

wherein:

R$_{11}$-R$_{15}$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino. Optionally, R$_{11}$ is alkyl (e.g., methyl). Optionally, R$_{14}$ is alkoxy (e.g., methoxy) or hydrogen. Optionally, R$_{12}$, R$_{13}$, and R$_{15}$ are hydrogen.

According to some embodiments of the invention, chemiluminescent agents comprising a 1,2-dioxetane moiety can be represented by the general formula:

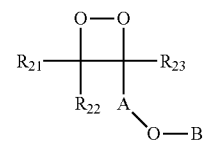

wherein: R$_{21}$ is selected from the group consisting of substituted or non-substituted cycloalkyl and heteroalicyclic, and R$_{22}$ is hydrogen; or R$_{21}$ and R$_{22}$ together form a substituted or non-substituted cycloalkyl or heteroalicyclic ring;

R$_{23}$ is alkoxy;

A is selected from the group consisting of substituted or non-substituted aryl and heteroaryl; and B is a moiety (e.g., a phosphate, a saccharide, a peptide) capable of being cleaved by an enzyme present in situ.

In some embodiments, the cycloalkyl is substituted or non-substituted adamantyl.

Thus, for example R$_{21}$ may be substituted or non-substituted adamantyl, or R$_{21}$ and R$_{22}$ together form substituted or non-substituted adamantyl (e.g., 2-adamantylidene). In some embodiments the adamantyl is substituted by halo (e.g., as defined herein), for example, by chloro (e.g., 5-chloro-2-adamantylidene).

According to some embodiments of the invention, a luciferase suitable for use in the context of embodiments of the present invention include, but is not limited to, firefly luciferase, *Latia* luciferase, *Omphalotus* luciferase, *Renilla* luciferase, bacterial luciferase, and aequorin.

The luciferin may be any compound suitable as a substrate for the luciferase for producing chemiluminescence. In some embodiments, the luciferin is the natural substrate of the luciferase (e.g., firefly luciferin for firefly luciferase).

According to some embodiments of the invention, oxalates which are suitable for use in the context of the present embodiments include ester and/or amide derivatives of oxalic acid, for example, a diester of oxalic acid (e.g., bis(pentafluorophenyl) oxalate, bis(2,4-dinitrophenyl) oxalate, bis(2,4,6-trichlorophenyl) oxalate), a diamide of oxalic acid (e.g., oxamide), and/or an oxalic acid derivative with an ester group and an amide group. The oxalate is optionally used in combination with a dye (e.g., a fluorescent and/or phosphorescent compound), for example, a dye which emits visible light (e.g., as fluorescence or phosphorescence).

According to a further aspect of some embodiments of the invention, there is provided a use of a chemiluminescent agent (e.g., as described herein) in the manufacture of a medicament for use in the treatment of a proliferative disease or disorder.

According to a further aspect of some embodiments of the invention, there is provided a chemiluminescent agent (e.g., as described herein), being identified for use in the treatment of a proliferative disease or disorder.

According to some embodiments of the above aspects, the treatment is devoid of administering a therapeutically effective amount of a photosensitizer in combination with the chemiluminescent agent (as defined herein).

In some embodiments, a treatment is devoid of administering a photosensitizer in combination with the chemiluminescent agent (as defined herein).

According to further aspects of some embodiments of the invention, there are provided methods, uses and compounds (which are also referred to herein as chemiluminescent agents) as described herein, for treating a proliferative disease or disorder, which utilize a compound having the general formula:

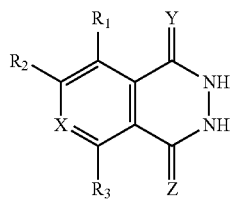

as such a compound is defined herein (e.g., with respect to chemiluminescent agents).

In some embodiments, a treatment (according to some embodiments of any of the abovementioned methods, uses and compounds as described herein) is devoid of administering a therapeutically effective amount of a photosensitizer in combination with the abovementioned compound (as defined herein).

In some embodiments, a treatment (according to some embodiments of any of the abovementioned methods, uses and compounds as described herein) is devoid of administering a photosensitizer in combination with the abovementioned compound (as defined herein).

Compounds of the above formula are also referred to herein as chemiluminescent agents, as it is believed that such compounds in general are chemiluminescent. However, compounds having the above formula and which are not chemiluminescent, if any exist, are not excluded from the scope of the invention.

In some embodiments, $R_1$ is hydroxy.

In some embodiments, $R_2$ is a substituted or non-substituted phenyl.

Without being bound by any particular theory, it is believed that compounds wherein $R_1$ is hydroxy and/or $R_2$ is phenyl are highly efficacious (e.g., when used as described herein), as such moieties are believed to contribute to the therapeutic effects of compounds having such moieties (e.g., as exemplified herein). Furthermore, as exemplified in Example 6 herein, SEM-009 (wherein $R_1$ is hydroxy) is more potent than the related compound SEM-007 (wherein $R_1$ is amino).

Hence, according to another aspect of some embodiments of the invention, there is provided a compound having the general formula:

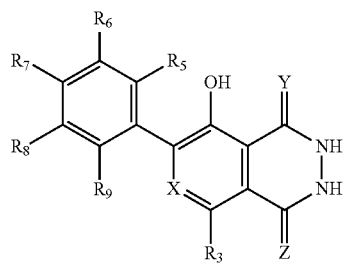

wherein:
X is N or $CR_4$;
Y and Z are each independently O or S; and
$R_3$-$R_9$ are each independently selected from the group consisting of hydrogen, alkyl, cycloalkyl, heteroalicyclic, aryl, heteroaryl, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, or, alternatively, any two of $R_3$-$R_9$ form a five- or six-membered alicyclic or aromatic ring, wherein at least one of $R_3$, $R_5$, $R_7$ and $R_9$ is selected from the group consisting of aryl, heteroaryl, halo, hydroxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine and amino, such that the compound comprises at least one of the aforementioned substituents.

It is to be appreciated that the above formula corresponds to a more general formula herein when $R_1$ of the more general formula is hydroxy, and $R_2$ of the more general formula is a phenyl moiety comprising the above variables $R_5$-$R_9$.

In some embodiments, X is N.

In some embodiments, at least one of $R_3$, $R_5$, $R_7$, and $R_9$ is selected from the group consisting of halo and hydrazine (e.g., a halo or hydrazine described herein).

In some embodiments, the phenyl is non-substituted, such that $R_5$-$R_9$ are each hydrogen. In such embodiments, $R_3$ is one of the aforementioned substituents (e.g., halo or hydrazine).

In some embodiments, $R_3$ is hydrogen. In such embodiments, the phenyl moiety is substituted, such that at least one of $R_5$, $R_7$ and $R_9$ is one of the aforementioned substituents.

In some embodiments wherein the phenyl moiety is substituted, $R_6$, $R_8$ and $R_9$ are each hydrogen, and at least one of $R_5$ and $R_7$ is a substituent (e.g., $R_5$ and/or $R_7$ is a substituent).

In some embodiments wherein the phenyl moiety is substituted, the substituent is halo.

In some embodiments, X is N, and at least one of $R_3$, $R_5$, $R_7$, and $R_9$ is selected from the group consisting of halo and hydrazine (e.g., a halo or hydrazine described herein).

In some embodiments, X is N, and $R_5$-$R_9$ are each hydrogen. In some such embodiments, $R_3$ is halo or hydrazine.

In some embodiments, X is N, and $R_3$ is hydrogen. In some embodiments, $R_6$, $R_8$ and $R_9$ are each hydrogen. In some embodiments, $R_5$ and/or $R_7$ is halo. Chloro is an exemplary halo phenyl substituent.

Each of the compounds described herein can further be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

In the context of some of the present embodiments, a pharmaceutically acceptable salt of the compounds described herein (e.g., L-012 or a structurally related compound) may optionally be a base addition salt comprising at least one group of the compound which is in a form of an anion, in combination with at least one counter ion (i.e., cation) that forms a pharmaceutically acceptable salt. Examples of suitable cations include metal cations of metals such as, but not limited to, sodium, potassium, magnesium, and calcium or ammonium.

Exemplary salts of L-012 or structurally related compounds are described in U.S. Pat. No. 5,420,275 and in EP 0491477, which are incorporated by reference as if fully set forth herein.

Each of these base addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

As used herein, the terms "amine" and "amino" refer to either a —NR'R" group, wherein R' and R" are selected from the group consisting of hydrogen, alkyl, cycloalkyl, heteroalicyclic (bonded through a ring carbon), aryl and heteroaryl (bonded through a ring carbon). R' and R" are bound via a carbon atom thereof. Optionally, R' and R" are selected from the group consisting of hydrogen and alkyl comprising 1 to 4 carbon atoms. Optionally, R' and R" are hydrogen.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein. Representative examples are piperidine, piperazine, tetrahydrofuran, tetrahydropyran, morpholine and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A disulfide bond describes a —S—S— bond.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"-group, where each of R' and R" is as defined herein.

A "carbamyl" or "carbamate" group encompasses O-carbamyl and N-carbamyl groups.

A carbamate bond describes a —O—C(=O)—NR'-bond, where R' is as described herein.

An "O-thiocarbamyl" group refers to an —OC(=S)—NR'R" group, where each of R' and R" is as defined herein.

An "N-thiocarbamyl" group refers to an R'OC(=S)NR"-group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'-bond, where R' is as described herein.

A "C-amido" group refers to a —C(=O)—NR'R" group, where each of R' and R" is as defined herein.

An "N-amido" group refers to an R'C(=O)—NR"-group, where each of R' and R" is as defined herein.

An "amide" group encompasses both C-amido and N-amido groups.

An amide bond describes a —NR'—C(=O)— bond, where R' is as defined herein.

A "urea" group refers to an —N(R)—C(=O)—NR"R''' group, where each of R' and R" is as defined herein, and R''' is defined as R' and R" are defined herein.

A "nitro" group refers to an —NO$_2$ group.

A "cyano" group refers to a —C≡N group.

The term "hydrazine" describes a —N(R')—N(R")R''' group, with each of R', R" and R''' as defined hereinabove.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"- group, with each of R' and R" as defined hereinabove.

According to some embodiments, the chemiluminescent agent described herein and/or any of the compounds utilized in any of the present embodiments is linked to a targeting moiety.

Herein, a "targeting moiety" refers to a moiety which is capable of bringing a compound (e.g., a chemiluminescent agent) linked to the targeting moiety into proximity with a target cell (e.g., a proliferating cell associated with the proliferative disease or disorder), wherein the proximity is such that the targeting moiety facilitates internalization of the compound into a target cell, and such that the compound may exert a therapeutic effect. Optionally, the targeting moiety attaches to the target. The targeting moiety is optionally a natural or synthetic peptide or polypeptide. Examples of such targeting moieties include, without limitation, transferrin, an antibody, and gonadotropin releasing hormone (GnRH).

In some embodiments, the compound (e.g., chemiluminescent agent) described herein is covalently attached to the targeting moiety, so as to result in a conjugate.

In some embodiments, the conjugate comprises a compound described herein which has a functional group covalently modified so as to be attached to the targeting moiety.

For example, a carboxy group in the compound may be covalently modified so as to form a conjugate having an amide bond, e.g., wherein the carboxy group is attached to an amine group of the functional moiety. Similarly, an amine group in the compound may be covalently modified so as to form a conjugate having an amide bond, e.g., wherein the amine group is attached to a carboxy group of the functional moiety.

Additional possibilities will be known to those of skill in the art for attaching a functional group of a compound described herein with a targeting moiety so as to produce a conjugate as described herein.

According to some embodiments, the chemiluminescent agent described herein and/or the compound described herein is encapsulated by a liposome. Optionally, the liposome is selected so as to target proliferating cells (e.g., cells associated with the disease or disorder described herein). For example, the liposomes may be of a size which allows them to leak out of a blood vessel of a tumor, but not out of a normal blood vessel. Optionally, the liposomes are about 200 nm or less in diameter.

According to a further aspect of embodiments of the invention, there is provided a conjugate comprising a chemiluminescent agent (e.g., as described herein) and/or the compound described herein, wherein the chemiluminescent agent (and/or compound) is covalently linked to a targeting moiety, the conjugate being identified for use in the treatment of a proliferative disease or disorder.

According to a further aspect of embodiments of the invention, there is provided a liposome (e.g., as described herein) comprising a chemiluminescent agent (e.g., as described herein) and/or the compound described herein, the liposome being identified for use in the treatment of a proliferative disease or disorder.

According to some embodiments of various aspects of embodiments of the invention described herein, the liposome described herein comprises a targeting moiety on a surface thereof, (e.g., a targeting moiety described herein).

In some embodiments, a targeting moiety is covalently attached to a liposome. Such attachment may be obtained in some embodiments by using techniques described herein (e.g., amide bond formation) for attaching a compound described herein to a targeting moiety.

According to any of the aspects of embodiments of the invention described herein, treatment may be effected by various routes of administration.

According to some embodiments, the administration of the chemiluminescent agent, compound, conjugate and/or liposome described herein is peri-tumor.

According to some embodiments, the administration of the chemiluminescent agent, compound, conjugate and/or liposome described herein is intravenous.

According to some embodiments, the administration of the chemiluminescent agent, compound, conjugate and/or liposome described herein is intraperitoneal.

According to some embodiments, the administration of the chemiluminescent agent, compound, conjugate and/or liposome described herein is oral.

According to some embodiments, the administration of the chemiluminescent agent, compound, conjugate and/or liposome described herein is transdermal (e.g., by application of a skin pad).

In any of the aspects of embodiments of the invention described herein, the active agent (e.g., the chemiluminescent agent, compound, conjugate and/or liposome described herein, and optionally a small amount of a photosensitizer, as described herein) can be used either per se, or as a part of a pharmaceutical composition which further comprises a pharmaceutically acceptable carrier, as defined herein.

Hence, according to a further aspect of embodiments of the invention, there is provided a pharmaceutical composition comprising a chemiluminescent agent described herein, a compound described herein, a conjugate comprising a chemiluminescent agent as described herein, and/or a liposome described herein, along with a pharmaceutically acceptable carrier.

As used herein a "pharmaceutical composition" refers to a preparation at least one active ingredient described herein with other chemical components such as pharmaceutically acceptable and suitable carriers and excipients. The purpose of a pharmaceutical composition is to facilitate administration of active ingredient(s) to an organism.

Hereinafter, the term "pharmaceutically acceptable carrier" refers to a carrier or a diluent that does not cause significant irritation to an organism and does not abrogate the biological activity and properties of the administered active ingredient(s). Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

In some embodiments, the at least one active agent in the composition includes at least one additional agent which is effective for treating the proliferative disease or disorder (e.g., an anti-cancer agent). The additional agent is not a photosensitizer in a therapeutically effective amount, as defined herein.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with embodiments of the present invention thus may be formulated in conventional manner using one or more pharmaceutically acceptable carriers comprising excipients and auxiliaries, which facilitate processing of the active ingredients (e.g., a chemiluminescent agent, compound, conjugate and/or liposome described herein) described herein into preparations which can be used pharmaceutically. Proper formulation is dependent upon the route of administration chosen.

For injection (e.g., intravenous injection, intraperitoneal injection), the active ingredients may be formulated as aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the active ingredients can be formulated readily by combining the active ingredients with pharmaceutically acceptable carriers well known in the art. Such carriers enable the active ingredients described herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of doses of an active ingredient(s).

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredients for use according to the present invention are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredients and a suitable powder base such as, but not limited to, lactose or starch.

The active ingredient(s) described herein may be formulated for parenteral administration, e.g., by bolus injection or continuous infusion (optionally peri-tumor). Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredient preparation in water-soluble form. Additionally, suspensions of the active ingredient(s) may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredient(s) to allow for the preparation of highly concentrated solutions.

Alternatively, active ingredient(s) may be in powder form for constitution with a suitable vehicle, e.g., sterile, pyrogen-free water, before use.

A pharmaceutical composition formulated for transdermal administration may optionally be present in a patch, a swab, a pledget, and/or a pad.

Transdermal pads, patches and the like may comprise some or all of the following components: a pharmaceutical composition (e.g., as described herein), a liner for protecting the patch during storage, which is optionally removed prior to use, an adhesive for adhering different components together and/or adhering the patch to the skin, a backing which protects the patch from the outer environment, and/or a membrane which controls release of an active ingredient into the skin.

Pharmaceutical compositions formulated for transdermal administration can be, for example, in a form of a cream, an ointment, a paste, a gel, a lotion, and a soap.

Ointments are semisolid preparations, typically based on vegetable oil (e.g. shea butter and/or cocoa butter), petrolatum or petroleum derivatives. As with other carriers or vehicles, an ointment base should be inert, stable, nonirritating and nonsensitizing.

Lotions are preparations that may to be applied to the skin without friction. Lotions are typically liquid or semiliquid preparations with a water or alcohol base, for example, an emulsion of the oil-in-water type. Lotions are typically preferred for treating large areas, due to the ease of applying a more fluid composition.

Creams are viscous liquids or semisolid emulsions, either oil-in-water or water-in-oil. Cream bases typically contain an oil phase, an emulsifier and an aqueous phase. The oil phase, also called the "lipophilic" phase, optionally comprises petrolatum and/or a fatty alcohol such as cetyl or stearyl alcohol. The aqueous phase optionally contains a humectant. The emulsifier in a cream formulation is optionally a nonionic, anionic, cationic or amphoteric surfactant.

Pastes are semisolid dosage forms which, depending on the nature of the base, may be a fatty paste or a paste made from a single-phase aqueous gel. The base in a fatty paste is generally petrolatum, hydrophilic petrolatum and the like. The pastes made from single-phase aqueous gels generally incorporate carboxymethylcellulose or the like as a base.

Gel formulations are semisolid, suspension-type systems. Single-phase gels contain organic macromolecules distributed substantially uniformly throughout the carrier liquid, which is typically aqueous, but also, preferably, contains a non-aqueous solvent and, optionally, an oil. Preferred organic macromolecules, i.e., gelling agents, are crosslinked acrylic acid polymers such as the family of carbomer polymers, e.g., carboxypolyalkylenes that may be obtained commercially under the trademark CARBOPOL™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

The active ingredient(s) described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose.

Determination of a therapeutically effective amount (as defined herein) is well within the capability of those skilled in the art, especially in light of the detailed disclosure provided herein.

For any chemiluminescent agent, compound, conjugate and/or liposome used in embodiments of the invention in combination (with or without a photosensitizer), the therapeutically effective amount or dose can be estimated initially from activity assays in animals. For example, a dose can be formulated in animal models to achieve a circulating concentration range that includes the $IC_{50}$, as determined by cell viability assays. Such information can be used to more accurately determine useful doses in humans.

Toxicity and therapeutic efficacy of the active ingredients described herein can be determined by standard pharmaceutical procedures in experimental animals, e.g., by determining the $LD_{50}$ (lethal dose causing death in 50% of the tested animals) for a subject active ingredient or combination of active ingredients. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active ingredients which are sufficient to maintain the desired effects. Such plasma levels will vary for each preparation, but can be estimated for any given active ingredient or combination of active ingredients from in vitro data, e.g., according to $IC_{50}$ values from cell viability assays. Dosages necessary to achieve a sufficient plasma level will depend on individual characteristics and route of administration. HPLC assays or bioassays can be used to determine plasma concentrations.

The amount of a composition to be administered will, of course, be dependent on the subject being treated, the severity of the affliction, the manner of administration, the judgment of the prescribing physician, etc.

Compositions of embodiments of the present invention may, if desired, be presented in a pack or dispenser device, such as an FDA (the U.S. Food and Drug Administration) approved kit, which may contain one or more unit dosage forms containing the active ingredients. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising active ingredients described herein formulated in a compatible pharmaceutical carrier may also be prepared, placed in an appropriate container, and labeled for treatment of an indicated disease or disorder, as is detailed hereinabove.

Thus, according to an embodiment of the present invention, the pharmaceutical compositions described herein are packaged in a packaging material and identified in print, in or on the packaging material, for use in the treatment of a proliferative disease or disorder (e.g., as described herein).

It is to be appreciated that suitable treatments utilizing each of the various active agents described herein are discussed herein in detail.

The phrase "proliferative disorder" describes any disease or disorder that involves abnormal cell proliferation. Examples include malignant, pre-malignant and benign tumors, including cancer.

The term "cancer" describes a tumor formed by abnormal growth of malignant cells. The term cancer encompasses primary or secondary tumors. The term "primary tumor" describes a tumor that is at the original site where it first arose and the term "secondary tumor" describes a tumor that has spread from its original (primary) site of growth to another site, close to or distant from the primary site.

The term "skin cancer" describes a cancer located on skin tissue and/or originating from the abnormal growth of skin cells. The term "mucosal cancer" describes a cancer located on mucosal tissue and/or originating from the abnormal growth of cells that make up the mucosal tissue. There are several types of skin cancers, the most common being basal cell carcinoma and squamous cell carcinoma, which are both non-melanoma skin cancers. Benign (non-cancerous) skin tumors may be present at birth or develop later.

Accordingly, exemplary skin and mucosal neoplastic tissues include, but are not limited to, keratoses (including, but not limited to, actinic keratosis, hydrocarbon keratosis, keratosis pilaris, seborrheic keratosis), nevi (including melanocytic nevi and epidermal nevi, with exemplary nevus listed hereinunder), archodrons, cysts, angiomas (such as hemangiomas, port-wine stains, lymphangiomas, and pyogenic granulomas), fibromas, fibrolipomas, condylomatas, lentigos, acanthomas, neurofibromas, hyperplasias, fibromas, warts (caused, for example, by viruses, e.g., verrucas), leiomyomas, syringomas, granulomas, xanthelasmas, cutaneous horns, Juvenile pseudomelanoma, basal cell carcinomas, basaliomas, Squamous cell carcinomas, Merkel-trabecular cell carcinomas, Nevus sebaceus of Jadassohn with basal cell carcinoma, kaposis sarcomas, oral visible lesions, papillomas, ibroepitheliomas, hyperplasias, hypertrophic Lesions, polyps, freckles, melasmas and melanomas.

Other types of cancers include solid malignant tumors such as, but not limited to, brain, ovarian, colon, prostate, kidney, bladder, breast, uterine, cervical and lung cancers. These cancers can be further broken down. For example, brain cancers include glioblastoma multiforme, anaplastic astrocytoma, astrocytoma, ependyoma, oligodendroglioma, medulloblastoma, meningioma, sarcoma, hemangioblastoma, and pineal parenchymal.

Non-limiting examples include, but are not limited to, acoustic neuroma, adenocarcinoma, angiosarcoma, astrocytoma, bile duct carcinoma, bladder carcinoma, thyroid cancer, tracheal cancer, bone originated tumor such as bone sarcoma, brain tumor such as glioma and neuroblastoma; breast cancer, cervical cancer, chondrosarcoma, chordoma, choriocarcinoma, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, hemangioblastoma, hepatic carcinoma, leiomyosarcoma, liposarcoma, lung carcinoma such as bronchogenic carcinoma, small cell lung carcinoma; lymphangioendotheliosarcoma, lymphangiosarcoma, medullary carcinoma, medulloblastoma, mesothelioma, myxosarcoma, pancreatic cancer, oligodendroglioma, osteogenic sarcoma, ovarian cancer, pancreatic carcinoma, papillary carcinoma, papillary adenocarcinoma, pinealoma, prostate cancer, rectal cancer, kidney cancer such as renal cell carcinoma and Wilms' tumor; retinoblastoma, rhabdomyosarcoma, sebaceous gland carcinoma, seminoma, stomach carcinoma, synovioma, sweat gland carcinoma, testicular tumor, uterus carcinoma, and metastatic disease of the respective primary cancer.

Additional examples include lymphomas, leukemias, and any other non-solid or semi-solid malignant tumors.

It is expected that during the life of a patent maturing from this application many relevant chemiluminescent agents will be developed and the scope of the term "chemiluminescent agent" is intended to include all such new technologies and agents a priori.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

MATERIALS AND METHODS

Materials:
2-Amino-2-(2-chlorophenyl)acetic acid was obtained from Sigma-Aldrich;
2-Amino-2-(4-chlorophenyl)acetic acid was obtained from Sigma-Aldrich;
2-Amino-2-phenylacetic acid ("Compound 1") was obtained from Sigma-Aldrich;
AMPPD (disodium 3-(4-methoxyspiro {1,2-dioxetane-3, 2'-(5'-chloro)tricyclo[3.3.1.1]decan}-4-yl)phenyl phosphate) was obtained from Suzhou Yacoo Chemical Reagent Corporation (China);

5-Hydroxy-2,3-dihydrophthalazine-1,4-dione (SEM-008) was prepared according to procedures described in the literature;

L-012 (SEM-007) was obtained from Waco Chemicals (Japan);

Lucigenin was obtained from Enzo Life Sciences (USA);

Luminol was obtained from Sigma-Aldrich;

Matrigel was obtained from BD Bioscience;

XTT (2,3-bis-(2-methoxy-4-nitro-5-sulfophenyl)-2H-tetrazolium-5-carboxanilide) was obtained from Beth Ha-Emek (Israel).

XTT assay kit was obtained from Biological Industries (Israel), and used as per the manufacturer's instructions.

All other reagents and solvents were obtained from Sigma Aldrich or other known vendors, unless otherwise indicated.

Cell Lines:

All cells were obtained from the ATCC (USA), and grown in an incubator at a temperature of 37° C. under an atmosphere of air with 5% $CO_2$. At 70-80% confluence, cells were centrifuged and counted All cell media contained either RPMI medium or Dulbecco's modified Eagle medium (DMEM), and were supplemented with 1% fetal bovine serum (FBS), antibiotics, and 2 mM L-glutamine.

Tumor Volume Evaluation:

Tumor volumes were quantified (in $cm^3$) at the indicated times by using the formula: tumor volume=($width^2 \times length$)/2. Tumor volume index or Progression Index refers to the ratio of a tumor volume at an indicated time to the first volume measured for that tumor.

Example 1

Effect of Increasing Dosages of L-012 on Cancer Cells (In Vivo Assays)

Nu/nu nude mice were inoculated on their right flank with $2 \times 10^6$ PC-3 prostate cancer cells in a Matrigel mixture. Following inoculation, two mice were treated with escalating concentrations of L-012 (also referred to herein as "SEM-007") by intraperitoneal injections twice per week, according to the following schedule:

Day 32-41.3 mg/kg L-012

Day 39-66.5 mg/kg L-012

Day 43-100.4 mg/kg L-012.

As a control, two mice were inoculated with PC-3 cells without receiving L-012.

The volume of the tumor was then monitored.

Figure 2:
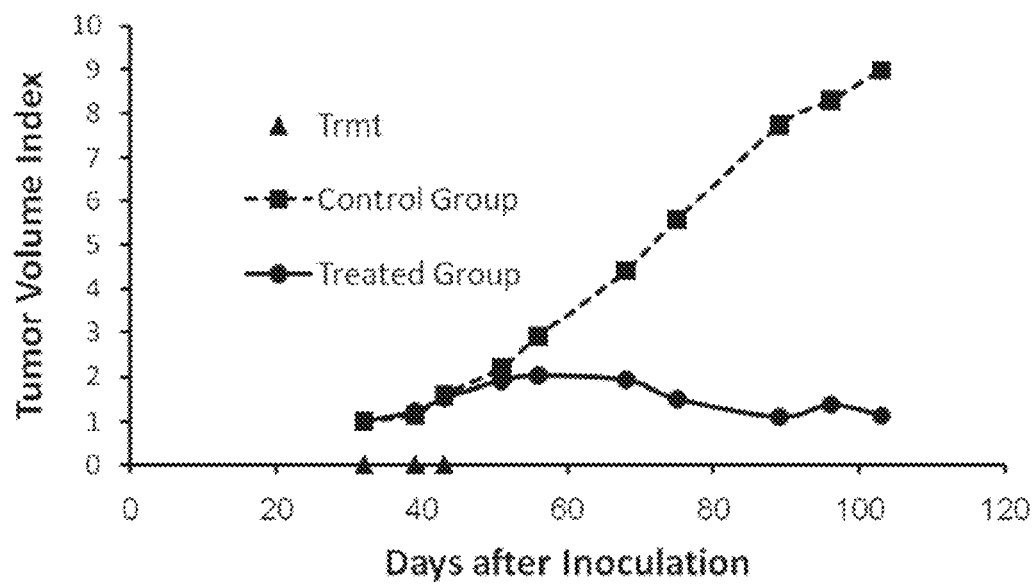
FIG. 2 is a graph showing the average tumor volume progression index (tumor volume relative to volume at 5 weeks) 5 to 15 weeks after inoculation of groups of nu/nu mice with human PC-3 prostate cancer cells; at the indicated time points (Trmt; triangles), the mice received an intraperitoneal injection of L012 (Treated Group; circles) or of vehicle only (Control Group; squares)

As shown in FIG. 2, administration of L-012 halted tumor progression, with no increase in average tumor volume occurring after L-012 administration. In contrast, the average tumor volume in the control group increased ten-fold over the same period.

These results indicate that L-012 is effective as an anti-cancer agent.

Example 2

Effect of Constant Dosages of L-012 on Cancer Cells (In Vivo Assays)

Nu/nu mice were inoculated with PC-3 cells as described in Example 1, and on days 25, 28, 32 and 35 post-inoculation the mice received an intraperitoneal injection of 200 µl of either phosphate buffer saline (PBS) or 41.3 mg/kg L-012 in PBS.

The tumor volume was measured periodically beginning on day 25 post-inoculation, and the weight loss over the course of the experiment was also measured.

Each treatment group and each control group consisted of four (and sometimes five) mice.

Figure 3A:
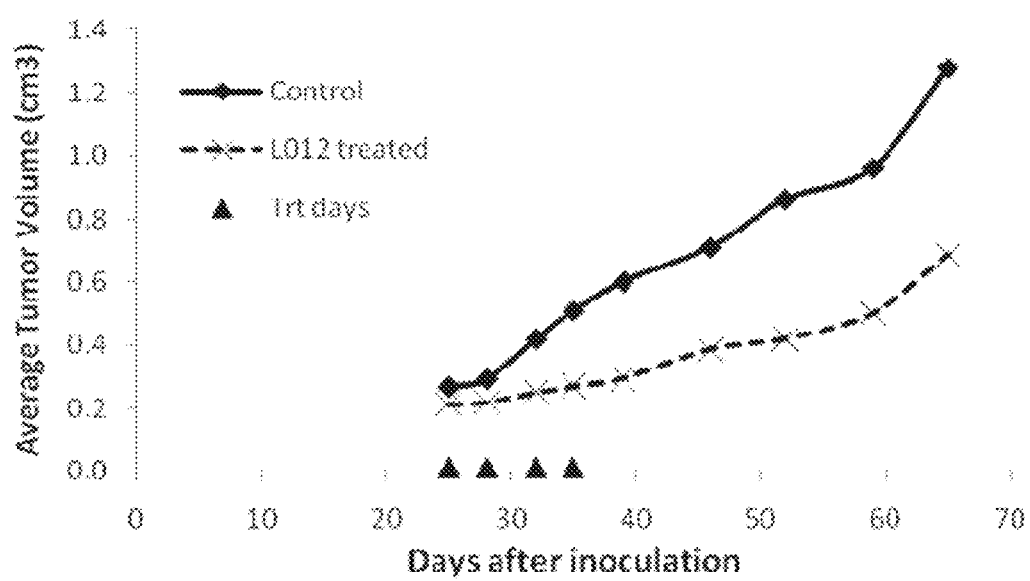
FIGS. 3A-3C present comparative plots graph showing the tumor volume 25 to 65 days after inoculation of nu/nu mice with PC-3 cancer cells, with (L012 treated; dashed line +x) or without (Control; diamonds) intraperitoneal injection of L-012 on days 25, 28, 32 and 35 after inoculation (Trt days; triangles) (FIG. 3A), the progression Index from the day of inoculation to day 90 post inoculation in nu/nu mice inoculated with PC-3 cancer cells and treated by ip injection of L012 (dashed line +triangles) or PBS (Control; diamonds) at the indicated days post inoculation (Trmt days; circles) (FIG. 3B), and the tumor volume 25 to 65 days after inoculation of nu/nu mice with PC-3 cancer cells, and ip injection of 43 mg/Kg L012 (L012 43; triangles), of 21 mg/Kg L012 (L012 21; dashed line +x) or of PBS (Control; diamonds) on days 28, 32, 42 and 49 after inoculation (Treatment days; circles) (FIG. 3C)

As shown in FIG. 3A, the treatment with L-012 reduced the tumor volume by 54% at day 65 in comparison with the PBS-treated control.

These results further indicate that L-012 is effective as an anti-cancer agent.

In another set of experiments, Nu/nu male mice, 1.5-month old, were injected subcutaneously on the right flank with PC-3 cells ($2.0 \times 10^6$ cells/mouse). On days 4, 8, 12, 15, 19, 36, 42 and 36(after the beginning of treatment), mice were treated with either vehicle (PBS) or 43 mg/Kg L012 by intraperitoneal injections. From the beginning of treatment, tumor dimensions were measured and tumor volume calculated. Progression Index was calculated as the ratio of tumor volume growth at a particular time point to the tumor volume at the initiation of treatment.

Figure 3B:
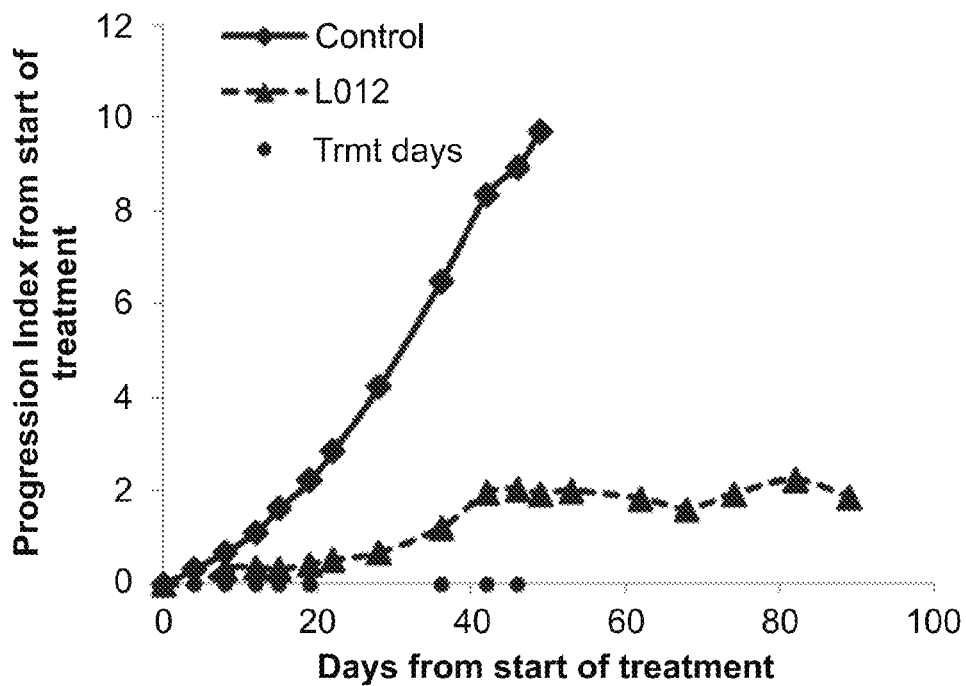

The results are present in FIG. 3B and show a sharp increase in the Progression Index in mice treated with L012, compared to non-treated mice.

In another set of experiments, C57/B16 male mice, 1.5-month old, were injected subcutaneously on the right flank with TRAMP C2 cells ($4.0 \times 10^6$ cells/mouse). On days 28, 32, 42 and 49, post inoculation, mice were treated by intraperitoneal injection with either vehicle (PBS) or 21 mg/Kg L012 or 43 mg/Kg of L012. From day 26, tumor dimensions were measured and tumor volume calculated.

Figure 3C:
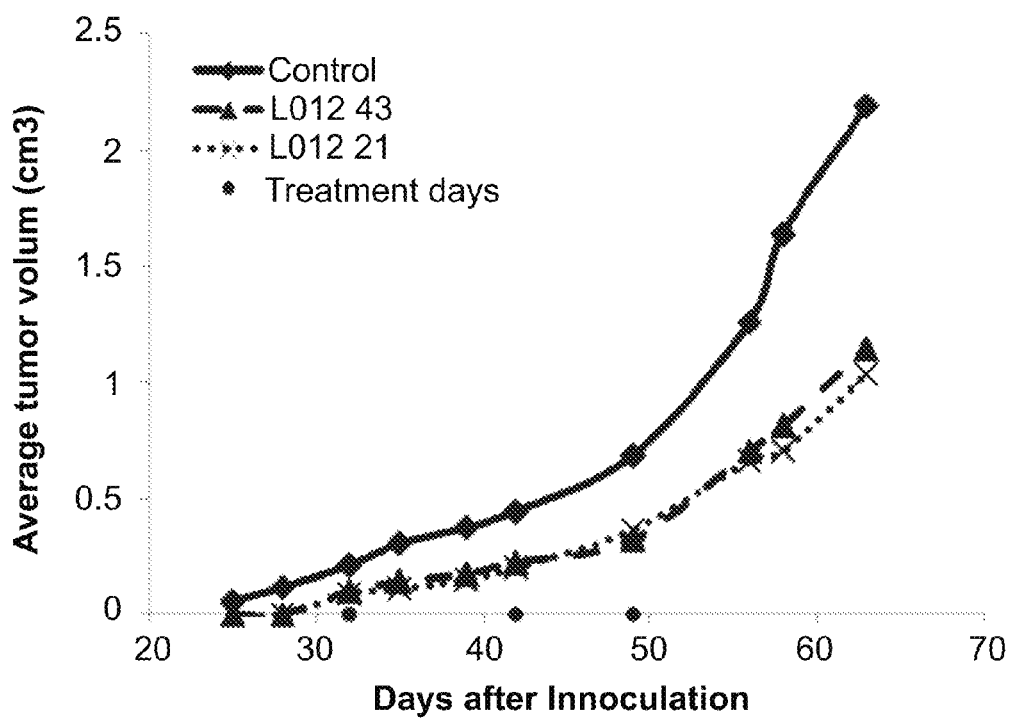

The results are present in FIG. 3C and show the similar effect of L012 in inhibiting tumor growth, at the two tested doses.

Example 3

Effect of Once Weekly and Twice Weekly Dosages of L-012 on Cancer Cells (In Vivo Assays)

Nu/nu mice were inoculated with PC-3 cells as described in Example 1, and on day 35 post-inoculation, the animals were divided into three groups.

Control animals received an intraperitoneal injection of PBS.

A second group received one weekly injection of 41.3 mg/kg L-012 for 3 weeks, i.e., on days 35, 42 and 49 post-inoculation. A third group received two weekly injections of 41.3 mg/kg L-012 for 3 weeks, i.e., on days 35, 36, 42, 47, 49 and 56.

The tumor volume was measured periodically beginning on day 35 post-inoculation.

Figure 4A:
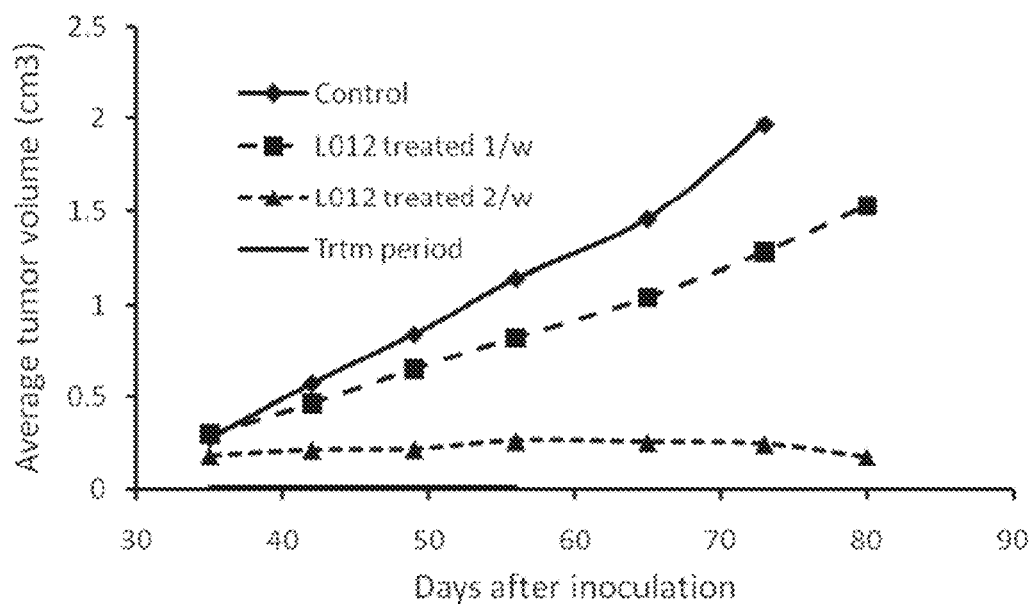
FIGS. 4A and 4B are graphs showing tumor volume (FIG. 4A) and the percent increase in tumor volume (FIG. 4B) 35 to 80 days after inoculation of nu/nu mice with PC-3 cancer cells, following intraperitoneal injection of L-012 once per week (L012 treated 1/w) or twice per week (L012 treated 2/w) during days 35-56 after inoculation (Trmt period), and without L-012 administration (Control)
Figure 4B:
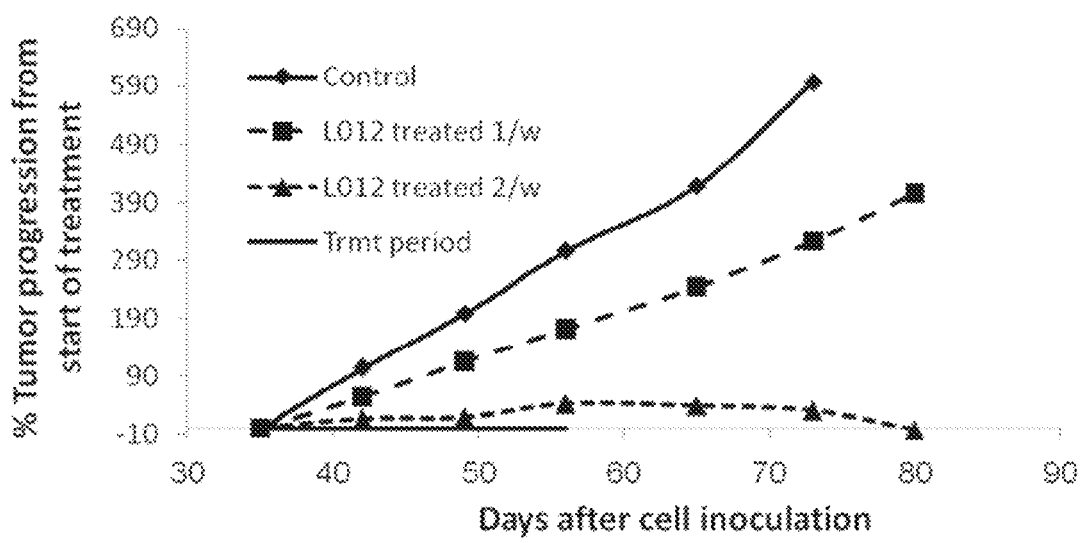
Figure 5:
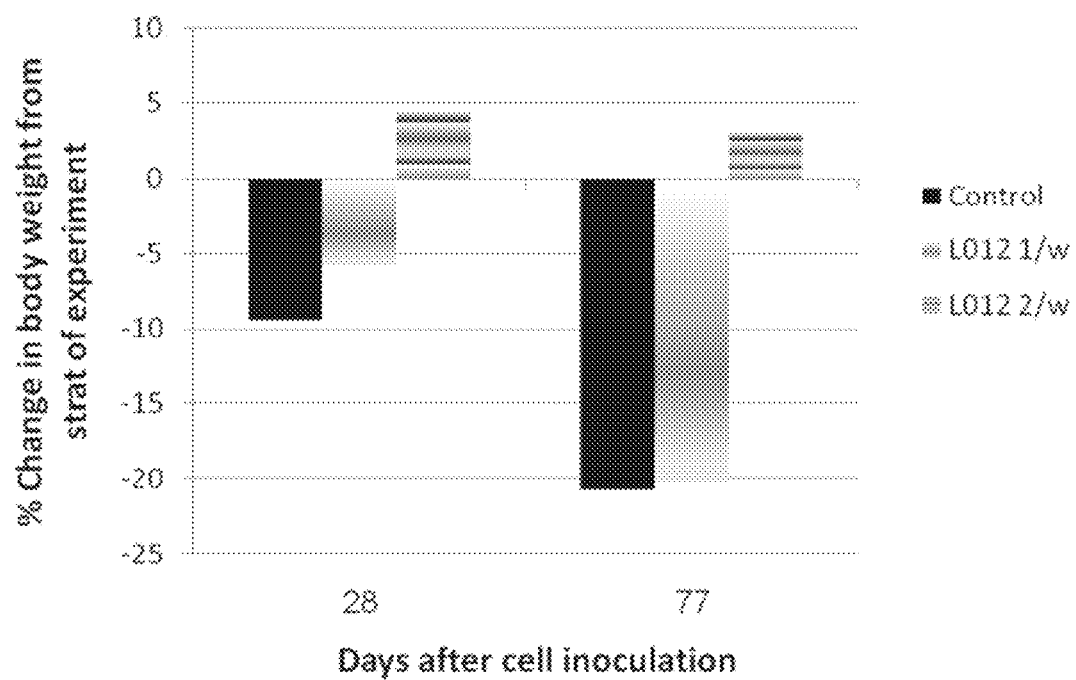
FIG. 5 is a bar graph showing the change in body weight of nu/nu mice 28 and 77 days after inoculation with PC-3 cells, following intraperitoneal injection of L-012 once per week (L012 1/w) or twice per week (L012 2/w) during days 35-56 after inoculation, and without L-012 administration (Control)

As shown in FIGS. 4A and 4B, administration of L-012 once per week reduced the tumor volume by 45% at day 73 in comparison with the PBS-treated control, whereas administration of L-012 twice per week reduced the tumor volume by 95%.

These results further indicate that L-012 inhibits tumor growth, in a dose-dependent manner.

As shown in FIG. 5, administration of L-012 one per week partially inhibited the decrease in body weight which occurred following inoculation with tumor cells, whereas administration of L-012 twice per week completely reversed the decrease in body weight.

These results confirm that L-012 inhibits tumor growth in a dose dependent manner, and further indicate that L-012 treatment in tumor-bearing mice does not result in systemic toxicity or morbidity.

Example 4

Preparation of Exemplary 2,3-Dihydropyridopyridazine-1,4-Dione Compounds

In view of the anti-cancer activity of SEM-007 (L-012) exemplified hereinabove, additional compounds having a 2,3-dihydropyridopyridazine-1,4-dione core were prepared and tested for anti-cancer activity. The structures of exemplary 2,3-dihydropyridopyridazine-1,4-dione compounds are shown in FIG. 6.

Preparation of SEM-009:

The compound SEM-009 (8-hydroxy-7-phenyl-2,3-dihydropyrido[4,3-d]pyridazine-1,4-dione, also referred to in the art as "L-002") was prepared as described in Scheme 1 below:

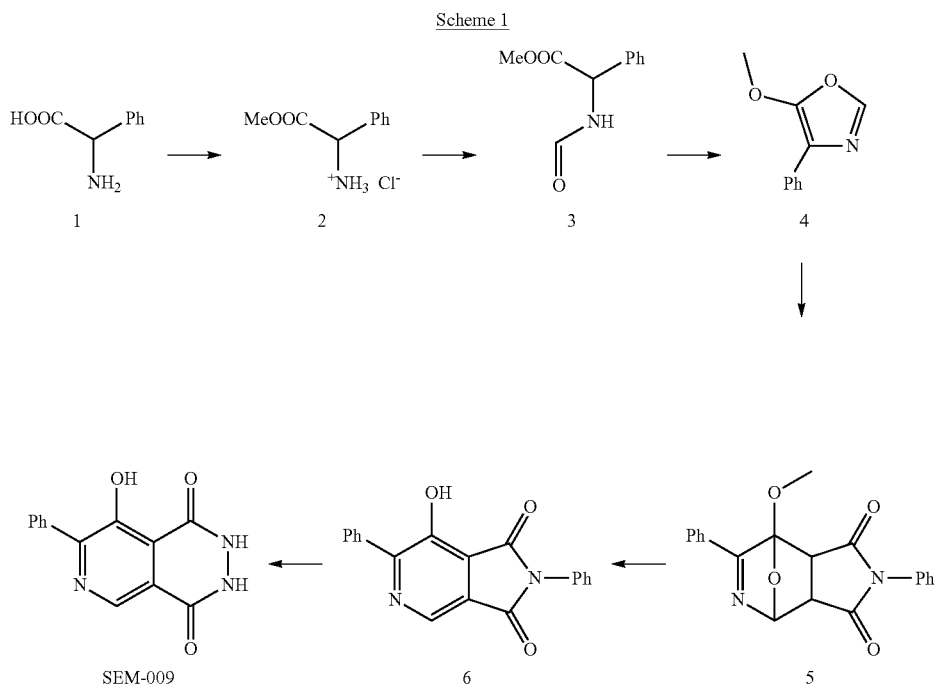

Scheme 1

A solution of 151 grams (1 mol) Compound 1 in 1.5 methanol was mixed with 2 molar equivalents (146 mL) of thionyl chloride (SOCl$_2$) at 0° C. under stirring. After 6 hours, the solvent was evaporated by vacuum to give Compound 2 in a quantitative yield.

20 ml of acetic anhydride was added to a solution of 21.5 grams (0.12 mol) of Compound 2 and 8.16 grams (0.12 mol) sodium formate in 200 ml of formic acid. After 2 hours, another 10 ml of acetic anhydride was added, and the mixture was stirred at a temperature of 50-60° C. for 2 hours. The solvent was then evaporated in vacuo. An aqueous solution of NaHCO$_3$ was then added, and the obtained residue was extracted with ethyl acetate. The obtained organic phase was dried over Na$_2$SO$_4$ and evaporated in vacuum to give 9.0 grams of pure Compound 3, which solidified with time, at a yield of 47%.

A mixture of Compound 3 (9.0 grams, 0.05 mol) and 32 grams (0.23 mol) P$_2$O$_5$ in 300 ml dichloromethane was heated at reflux overnight, and NaHCO$_3$ was then added. The aqueous layer was then extracted with dichloromethane. The resulting organic layer was dried over Na$_2$SO$_4$ and evaporated in vacuo to provide crude Compound 4. Purification by flash column chromatography gave 3 grams of pure Compound 4, at a yield of 34%.

A solution of Compound 4 (3 grams, 17 mmol) and 4.5 grams (26 mmol) N-phenylmaleimide in 50 ml toluene was heated at reflux for 6 hours. The solvent was evaporated to give 5.9 grams of crude Compound 5.

Number of batches were prepared and the compound was used without further purification.

A solution of compound 5 (22 grams, 63 mmol) in 50 ml ethanol with 0.3 ml of concentrated HCl was heated at reflux for 1 hour. After cooling to room temperature, a precipitate formed and was filtered to give 3 grams of Compound 6, at a yield of 15%.

Compound 6 (3 grams, 9 mmol) was dissolved in 50 ml of hydrazine hydrate (N$_2$H$_4$·H$_2$O) and the reaction mixture was heated at a temperature of 120° C. for 1 hour. The solvent was evaporated in vacuo and ethanol was added to the obtained residue. The resulting crystals were filtered off and re-suspended in water. The suspension was then stirred, and the pH of the solution was adjusted to a value in a range of 1-2 using 10% aqueous HCl. The obtained product was filtered to give 1.6 gram of SEM-009 as a yellow powder, at a yield of 66%.

The identity of the obtained compound was confirmed by NMR spectroscopy (500 MHz), and by mass spectroscopy.

The mass spectrum showed m/e values of 256.0 for a positive ion, and 253.8 for a negative ion, which corroborates the structure of SEM-009.

Preparation of SEM-011:

The compound SEM-011 (5-hydrazinyl-8-hydroxy-7-phenyl-2,3-dihydropyrido[4,3-d]pyridazine-1,4-dione) was prepared as described in Scheme 2 below:

Scheme 2

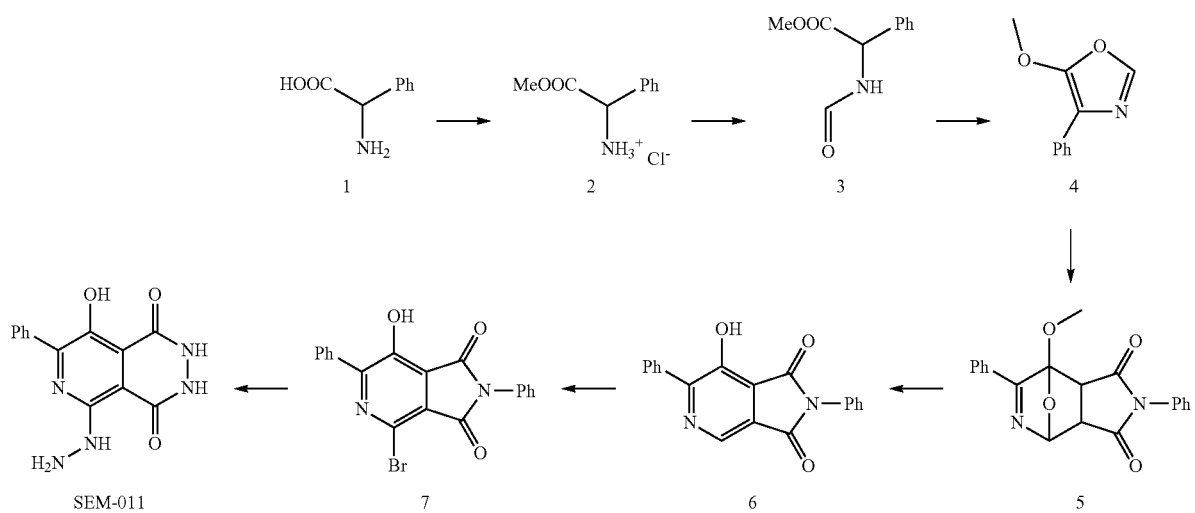

Compound 6 was prepared as described hereinabove, and 1.5 gram of Compound 6 was dissolved in DMF (dimethylformamide), and 0.85 gram of NBS (N-bromosuccinimide) was then added portionwise. The resulting mixture was stirred at ambient temperature overnight. The solvent was then evaporated and the obtained residue was purified by flash chromatography using dichloromethane:methanol (80:1) to give 0.78 gram of Compound 7.

Compound 7 (0.7 gram) was dissolved in 20 ml of hydrazine hydrate ($N_2H_4.H_2O$) and heated at a temperature of 120° C. for 1 hour. The solvent was evaporated and ethanol was added to the obtained residue. The resulting crystals were filtered and suspended in water. The suspension was then stirred and the pH adjusted to a range of 1-2 with 10% aqueous HCl. After stirring for 1 hour, the resulting crystals were filtered to give crude Compound 7 as a yellow powder. 60 mg of SEM-011 was isolated by performing several recrystallizations from acetic acid.

The structure of the obtained compound was verified by NMR (500 MHz), and by mass spectroscopy.

Preparation of SEM-013:

The compound SEM-013 (8-hydroxy-7-(2-chlorophenyl)-2,3-dihydropyrido[4,3-d]pyridazine-1,4-dione) was prepared in accordance with the procedures described hereinabove for preparing SEM-009, except that 2-amino-2-(2-chlorophenyl)acetic acid was used as a starting material instead of 2-amino-2-phenylacetic acid (Compound 1).

The structure of the obtained compound was verified by NMR spectroscopy (500 MHz), and by mass spectroscopy.

The mass spectrum showed m/e values of 290.0 for a positive ion, and 288.0 for a negative ion, which corroborates the structure of SEM-013.

Preparation of SEM-014:

The compound SEM-014 (8-hydroxy-7-(4-chlorophenyl)-2,3-dihydropyrido[4,3-d]pyridazine-1,4-dione) was prepared in accordance with the procedures described hereinabove for preparing SEM-009, except that 2-amino-2-(4-chlorophenyl)acetic acid was used as a starting material instead of 2-amino-2-phenylacetic acid (Compound 1).

The structure of the obtained compound was verified by NMR spectroscopy (500 MHz), and by mass spectroscopy.

NMR (DMSO-$d_6$): δ=8.68 (s, 1H), 8.22 (d, J=10 Hz), 2H), 7.55 (d, J=10 Hz) 2H).

The mass spectrum showed m/e values of 292.0 and 293.0 (10:3:1 ratio, isotopes of Cl) for a positive ion, and 288.0, 291.0 (10:3:1 ratio, isotopes of Cl) for a negative ion, which corroborates the structure of SEM-014.

Example 5

Effect of SEM-011 on Cancer Cells (In Vitro Assays)

The compound SEM-011 was tested for anti-cancer activity, using the PC-3 prostate cancer cell line. Cells were grown in full culture medium for 24 hours. The medium was then removed and cells were washed with PBS. The PBS was then replaced by fresh medium containing different concentrations of SEM-011 in a range of 50 to 800 μM, or with SEM-011-free medium as a control. Cells were then cultured for 24 hours, after which time the level of cellular metabolism in the cultures was measured using a standard XTT (2,3-bis-(2-methoxy-4-nitro-5-sulfophenyl)-2H-tetrazolium-5-carboxanilide) assay. Growth inhibition was evaluated by calculating the percent decrease in absorbance in SEM-011-treated test cultures as compared to control cultures.

TABLE 1

Growth inhibition in PC-3 cancer cells as a function of SEM-011 concentration

| | SEM-011 concentration (μM) | | | | |
|---|---|---|---|---|---|
| | 50 | 100 | 200 | 400 | 800 |
| Growth inhibition (%) | 50 | 87 | 96 | 96 | 96 |

As shown in Table 1, SEM-011 almost completely inhibited PC-3 cell growth at concentrations of 200 μM or more, and exhibited 50% growth inhibition at a concentration of 50 μM.

These results indicate that SEM-011 exhibits considerable anti-cancer activity.

Example 6

Effect of SEM-007 (L-012) and SEM-009 on Cancer Cells (In Vitro Assays)

The compounds SEM-007 (also referred to herein and in the art as "L-012") and SEM-009 (also referred to in the art as "L-002") were tested for anti-cancer activity using a variety of cell lines. The cell lines used were OvCar-3 ovarian cancer cells, SKOV-3 ovarian cancer cells, HepG2 liver cancer cells, PC-3 prostate cancer cells, and CHRF acute myeloid leukemia cells. Growth inhibition was determined for a variety of concentrations of each tested compound in accordance with procedures described in Example 5, except that cells were incubated with the tested agent for 72 hours, and the concentration which resulted in 50% growth inhibition (IC50) was calculated using standard formulas.

As shown in FIG. 7, SEM-007 and SEM-009 both exhibited significant growth inhibition towards all of the tested cell lines, with the IC50 of SEM-007 being between 130 μM and 300 μM, and the 1050 of SEM-009 being between 40 μM and 200 μM. The IC50 of SEM-009 was lower than that of SEM-007 in all of the tested cell lines.

These results confirm that SEM-007 (L-012) exhibits considerable anti-cancer activity, and further indicates that SEM-009 is even more potent than SEM-007.

Example 7

Effect of Exemplary Chemiluminescent Agents on Cancer Cells

The above results indicate that the chemiluminescent agent L-012 (SEM-007) and related compounds exhibit considerable anti-cancer activity. Additional chemiluminescent agents were therefore tested for anti-cancer activity, in order to ascertain whether anti-cancer activity is a general property of chemiluminescent agents. The tested chemiluminescent agents, SEM-008 (5-hydroxy-2,3-dihydrophthalazine-1,4-dione), AMPPD, luminol, lucigenin and MCLA, represent a variety of structural families of chemiluminescent agents, as can be seen, for example, in FIG. 1.

Anti-cancer activity was determined by measuring growth inhibition of CHRF line acute myeloid leukemia (AML) cells treated with 800 μM of each compound, according to procedures described in Example 5, except that cells were incubated with the tested agent for 72 hours.

TABLE 2

Growth inhibition in AML cancer cells by various chemiluminescent agents

| | Compound (80 μM) | | | | |
|---|---|---|---|---|---|
| | SEM-008 | AMPPD | Luminol | Lucigenin | MCLA |
| Growth inhibition (%) | 42 | 25 | 40 | 33 | 85 |

As shown in Table 2, all of the tested chemiluminescent agents inhibited AML cell growth, with MCLA being particularly potent (85% growth inhibition).

These results indicate that chemiluminescent agents in general exhibit anti-cancer activity.

In additional sets of experiments, PC-3 cells were cultured for 24, 48 or 73 hours either with culture medium alone (control) or with different concentrations of various chemiluminescent agents. At the end of the culture period, the level of mitochondrial metabolism was measured (using Alamar Blue assay) and the activity of the chemiluminescent agents was determined by percents of growth inhibition; the inhibition of growth in treated cell cultures compared to non-treated, control cells.

The results are presented in Table 3 below, as % growth inhibition measured at each of the tested conditions, and clearly show that all the tested chemoliminescent agents exhibit substantial growth inhibition, further demonstrating the anti-proliferative effect of chemiluminescent agents as described herein.

TABLE 3

| | SEM-007 | | | SEM-009 | | | SEM-013 | | | SEM-014 | | | SEM-015 | | |
|---|---|---|---|---|---|---|---|---|---|---|---|---|---|---|---|
| | | | | | | | time | | | | | | | | |
| | 24 hrs | 48 hrs | 73 hrs | 24 hrs | 48 hrs | 73 hrs | 24 hrs | 48 hrs | 72 hrs | 24 hrs | 48 hrs | 72 hrs | 24 hrs | 48 hrs | 72 hrs |
| Conc. 800 uM | 73.80 | 78 | 90 | 89.1 | 85.7 | 89.0 | 37.13 | 55.499 | 64.159 | 54.265 | 71.304 | 76.1153 | 20.913 | 16.944 | 11.914 |
| Conc. 400 uM | 77.73 | 70 | 76 | 90.6 | 83.7 | 85.6 | 30.098 | 29.124 | 41.652 | 55.688 | 70.464 | 72.6677 | 7.065 | 12.85 | 11.153 |
| Conc. 200 uM | 66.84 | 58 | 58.0 | 84.2 | 80.3 | 80.5 | 23.781 | 22.329 | 23.056 | 51.587 | 71.895 | 68.2256 | 15.735 | 30.383 | 10.753 |
| Conc. 100 uM | 65.25 | 38 | 38 | 81.4 | 49.2 | 47.8 | | | | | | | | | |
| Conc. 50 uM | 46.46 | 31 | 20 | −27.2 | 26.6 | 21.3 | | | | | | | | | |
| Conc. 25 uM | | 27 | 11 | | | | | | | | | | | | |
| Est IC50 (uM) | | 160 | 140 | | | | | 100 | 110 | | | | | | |

Example 8

Effect of SEM 009 on Cancer Cells (In Vivo Data)

Nu/nu male mice, 1.5-month old, were injected subcutaneously on the right flank with PC-3 cells (2.0×10⁶ cells/mouse). On days 4, 8, 12, 15, 19, 36, 42 and 46 (after beginning of treatment), mice were treated with either vehicle (PBS) or 43 mg/Kg SEM 009, by intravenous injection, as indicated.

From the beginning of treatment, tumor dimensions were measured and tumor volume calculated. Progression Index was calculated as the ratio of tumor volume growth at a particular time point to the tumor volume at the initiation of treatment.

Figure 9:
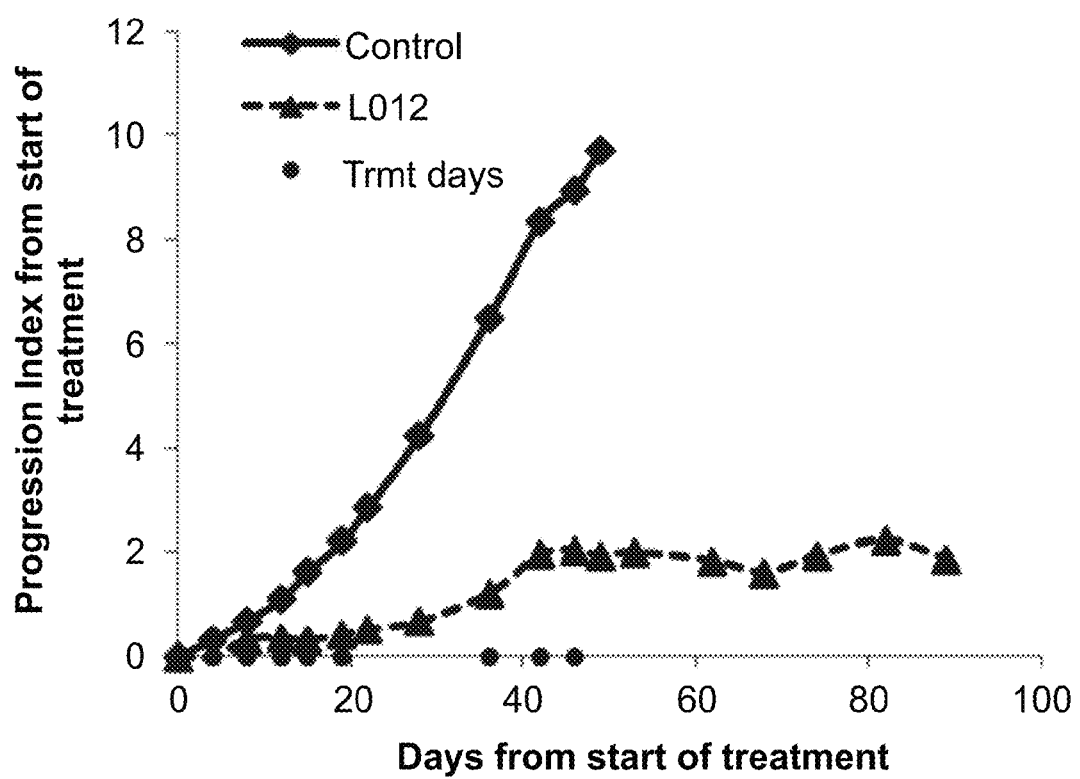
FIG. 9 is a graph showing the progression index from the day of inoculation to day 90 post inoculation in nu/nu mice inoculated with PC-3 cancer cells and treated by i.p. injection of SEM-009 (dashed line+triangles) or PBS (Control; diamonds) at the indicated days post inoculation (Trmt days; circles).

The results are present in FIG. 9 and show a sharp decrease in the Progression Index in mice treated with SEM 009, compared to non-treated mice, thereby further demonstrating the therapeutic effect of chemiluminescence compounds of this family.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of inhibiting proliferation of cancer cells in a subject in need thereof, the method comprising administering to the subject a chemiluminescent agent, thereby inhibiting said proliferation of cancer cells, the method being devoid of administering a therapeutically effective amount of a photosensitizer in combination with said chemiluminescent agent, wherein said chemiluminescent agent is:

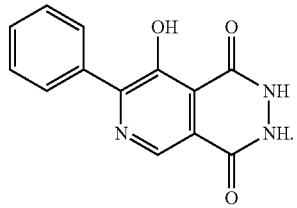 [SMILES: O=c1[nH][nH]c(=O)c2c(O)c(-c3ccccc3)ncc12]

2. The method of claim 1, being devoid of administering a photosensitizer in combination with said chemiluminescent agent.

3. The method of claim 1, wherein said chemiluminescent agent is coupled to a targeting moiety.

4. The method of claim 1, wherein said chemiluminescent agent is encapsulated by a liposome.

5. The method of claim 4, wherein said liposome comprises a targeting moiety attached on a surface thereof.

6. A method of inhibiting proliferation of cancer cells in a subject in need thereof, the method comprising administering to the subject a therapeutically effective amount of a compound having the formula:

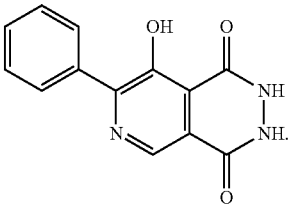 [SMILES: O=c1[nH][nH]c(=O)c2c(O)c(-c3ccccc3)ncc12]

thereby inhibiting said proliferation of cancer cells.

7. The method of claim 6, wherein said compound is coupled to a targeting moiety.

8. The method of claim 6, wherein said compound is encapsulated by a liposome.

9. The method of claim 8, wherein said liposome comprises a targeting moiety attached to a surface thereof.

10. The method of claim 1, further comprising administering at least one additional agent which is effective for inhibiting said proliferation of cancer cells.

11. The method of claim 6, further comprising administering at least one additional agent which is effective for inhibiting proliferation of cancer cells.

* * * * *